US008187878B2

(12) United States Patent
Dalton et al.

(10) Patent No.: US 8,187,878 B2
(45) Date of Patent: May 29, 2012

(54) METHODS FOR INCREASING DEFINITIVE ENDODERM DIFFERENTIATION OF PLURIPOTENT HUMAN EMBRYONIC STEM CELLS WITH PI-3 KINASE INHIBITORS

(75) Inventors: Stephen Dalton, Athens, GA (US); Allan Sheppard, Cambridge (NZ); Karen Jones, Heidelberg (AU); E. Edward Baetge, Encinitas, CA (US); Kevin A. D'Amour, San Diego, CA (US); Alan D. Agulnick, San Marcos, CA (US)

(73) Assignees: University of Georgia Research Foundation, Inc., San Diego, CA (US); ViaCyte, Inc., San Diego, CA (US)

( * ) Notice: Subject to any disclaimer, the term of this patent is extended or adjusted under 35 U.S.C. 154(b) by 111 days.

(21) Appl. No.: 11/573,662

(22) PCT Filed: Aug. 15, 2005

(86) PCT No.: PCT/US2005/028829
§ 371 (c)(1),
(2), (4) Date: Jul. 24, 2007

(87) PCT Pub. No.: WO2006/020919
PCT Pub. Date: Feb. 23, 2006

(65) Prior Publication Data
US 2007/0281355 A1 Dec. 6, 2007

Related U.S. Application Data

(60) Provisional application No. 60/601,664, filed on Aug. 13, 2004.

(51) Int. Cl.
*C12N 5/00* (2006.01)
*C12N 5/075* (2010.01)
(52) U.S. Cl. .......... 435/377; 435/325; 435/366; 514/8.9
(58) Field of Classification Search .................. 435/377, 435/325, 366; 514/8.9
See application file for complete search history.

(56) References Cited

U.S. PATENT DOCUMENTS

| | | |
|---|---|---|
| 5,453,357 A | 9/1995 | Hogan |
| 5,670,372 A | 9/1997 | Hogan |
| 5,690,926 A | 11/1997 | Hogan |
| 5,817,637 A | 10/1998 | Weiner et al. |
| 5,830,876 A | 11/1998 | Weiner et al. |
| 5,843,780 A | 12/1998 | Thomson |
| 6,015,671 A | 1/2000 | Field |
| 6,090,622 A | 7/2000 | Gearhart et al. |
| 6,165,993 A | 12/2000 | Herrmann et al. |
| 6,200,806 B1 | 3/2001 | Thomson |
| 6,251,671 B1 | 6/2001 | Hogan et al. |
| 6,261,281 B1 | 7/2001 | Mathiesen et al. |
| 6,458,589 B1 | 10/2002 | Rambhatla et al. |
| 6,506,574 B1 | 1/2003 | Rambhatla et al. |
| 6,872,389 B1 | 3/2005 | Faris |
| 6,921,811 B2 | 7/2005 | Zamora et al. |
| 7,033,831 B2 | 4/2006 | Fisk et al. |
| 7,153,684 B1 | 12/2006 | Hogan |
| 7,256,042 B2 | 8/2007 | Rambhatla et al. |
| 7,326,572 B2 | 2/2008 | Fisk et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,695,963 B2 | 4/2010 | Agulnick et al. |
| 7,695,965 B2 | 4/2010 | Martinson et al. |
| 7,704,738 B2 | 4/2010 | D'Amour |
| 2002/0019046 A1 * | 2/2002 | Carpenter et al. ............ 435/368 |
| 2002/0072117 A1 | 6/2002 | Xu et al. |
| 2002/0090723 A1 | 7/2002 | Carpenter et al. |
| 2003/0138948 A1 | 7/2003 | Fisk et al. |
| 2003/0175956 A1 | 9/2003 | Bodnar et al. |
| 2003/0190748 A1 | 10/2003 | Thomson |
| 2003/0224411 A1 | 12/2003 | Stanton et al. |
| 2004/0127406 A1 | 7/2004 | Presnell et al. |
| 2004/0229350 A1 | 11/2004 | Strelchenko et al. |
| 2006/0003446 A1 | 1/2006 | Keller |
| 2006/0019387 A1 | 1/2006 | Faris |
| 2006/0040385 A1 | 2/2006 | Itskovitz-Eldor et al. |
| 2006/0040387 A1 | 2/2006 | Fisk et al. |
| 2006/0128018 A1 | 6/2006 | Zwaka |

(Continued)

FOREIGN PATENT DOCUMENTS

AU 2003304106 11/2004

(Continued)

OTHER PUBLICATIONS

Chambers et al. 2004. Self-renewal of teratocarcinoma and embryonic stem cells. Oncogene (2004) 23, 7150-7160.*
R&D systems, Cytokine bulletin 2007: TGF-beta Superfamily Signaling in ES cells (Mice are Not Men) p. 1-3.*
Carpenter et al., 1996, "Phosphoinositide Kinases," Curr. Opin. Cell Biol., 8(2):153-158.
Chung et al., 1994, "PDGF- and Insulin-Dependent pp70S6k Activation Mediated by Phosphatidylinositol-3-OH Kinase," Nature, 370:71-75.
D'Amour et al., 2005, "Efficient Differentiation of Human Embryonic Stem Cells to Definitive Endoderm," Nature Biotechnology, 23(12):1534-1541.

(Continued)

*Primary Examiner* — Taeyoon Kim
(74) *Attorney, Agent, or Firm* — The Law Office of Jane K. Babin, Professional Corporation; Jane K. Babin

(57) ABSTRACT

The present invention provides compositions and methods for the production of differentiated mammalian cells. More particularly, the present invention provides cellular differentiation methods employing culturing the cells on a feeder layer or under feeder-free conditions in cell culture and further contacting the cells with an inhibitor of the PI3-kinase pathway and a member of the TGFb family for the generation of differentiated mammalian cells from pluripotent mammalian stem cells. Preferably, the differentiated cell is selected from the group consisting of a mesendodermal cell, a mesodermal cell, and an endodermal cell.

19 Claims, 14 Drawing Sheets

U.S. PATENT DOCUMENTS

| | | | |
|---|---|---|---|
| 2006/0148081 | A1 | 7/2006 | Kelly et al. |
| 2006/0276420 | A1 | 12/2006 | Keller et al. |
| 2007/0004038 | A1 | 1/2007 | D'Amour et al. |
| 2007/0122905 | A1 | 5/2007 | D'Amour et al. |
| 2007/0259421 | A1 | 11/2007 | D'Amour et al. |
| 2007/0281355 | A1 | 12/2007 | Dalton et al. |
| 2008/0113433 | A1 | 5/2008 | Robins et al. |
| 2008/0268534 | A1 | 10/2008 | Robins et al. |
| 2009/0104696 | A1 | 4/2009 | Robins et al. |
| 2009/0298178 | A1 | 12/2009 | D'Amour |

FOREIGN PATENT DOCUMENTS

| | | |
|---|---|---|
| EP | 1298201 | 4/2003 |
| WO | WO97/32033 | 9/1997 |
| WO | WO-9818943 | 5/1998 |
| WO | WO98/43679 | 10/1998 |
| WO | WO-9913915 | 3/1999 |
| WO | WO99/53021 | 10/1999 |
| WO | WO00/27995 | 5/2000 |
| WO | WO-0029442 | 5/2000 |
| WO | WO-0210347 | 2/2002 |
| WO | WO-0234880 | 5/2002 |
| WO | WO-02059278 | 8/2002 |
| WO | WO-03050249 | 6/2003 |
| WO | WO-03100026 | 12/2003 |
| WO | WO-2004098490 | 11/2004 |
| WO | WO-2005017131 | 2/2005 |
| WO | WO-2005033294 | 4/2005 |
| WO | WO-2005045001 | 5/2005 |
| WO | WO-2005063971 | 7/2005 |
| WO | WO-2005097977 | 10/2005 |
| WO | WO-2005097980 | 10/2005 |
| WO | WO-2005116073 | 12/2005 |
| WO | WO-2006016999 | 2/2006 |
| WO | WO-2006017134 | 2/2006 |
| WO | WO-2006020919 | 2/2006 |
| WO | WO-2006034873 | 4/2006 |
| WO | WO-2006083782 | 8/2006 |
| WO | WO-2007002210 | 1/2007 |
| WO | WO 2007/103282 | 9/2007 |

OTHER PUBLICATIONS

Hori et al., 2002, "Growth Inhibitors Promote Differentiation of Insulin-Producing Tissue from Embryonic Stem Cells," PNAS, vol. 99(25)16105-16110.

James et al., 2005, "TGFb/Activin/Nodal Signaling is Necessary for the Maintenance of Pluripotency in Human Embryonic Stem Cells," Development, 132:1273-1282.

Kumar et al., 2003, "Signals from Lateral Plate Mesoderm Instruct Endoderm Toward a Pancreatic Fate," Development Biology, 259:109-122.

Takahashi et al., 2003, "Role of ERas in Promoting Tumour-Like Properties in Mouse Embryonic Stem Cells," Nature, 423:541-545.

Qi et al., 2004, "BMP4 Supports Self-Renewal of Embryonic Stem Cells by Inhibiting Mitogen-Activated Protein Kinase Pathways," PNAS, 101(16):6027-6032.

Kubo et al., 2004, "Development of Definitive Endoderm from Embryonic Stem Cells in Culture," Development, 131 (7):1651-1662.

Abe, et al.,"Endoderm-Specific Gene Expression in Embryonic Stem Cells Differentiated to Embryoid Bodies," Exp Cell Res. 229:27-34,1996.

Alexander, et al., "A molecular pathway leading to endoderm formation in zebrafish," Curr Biol. 9:1147-57,1999.

Alexander, et al., "Casanova plays an early and essential role in endoderm formation in zebrafish," Dev Biol. 215:343-57,1999.

Ang, et al., "HNF-3beta is essential for node and notochord formation in mouse development," Cell 78:561-574,1994.

Ang, et al., "The Formation and Maintenance of the Definitive Endoderm Lineage in the Mouse: Involvement of HNF3/forkhead Proteins," Development. 119:1301-1315.,1993.

Aoki, et al., "Regulation of nodal signalling and mesendoderm formation by TARAM-A, a TGFbeta-related type I receptor.," Dev Biol. 241:273-88,2002.

Armstrong, et al., "The role of PI3K/AKT, MAPK/ERK and NF kappa beta signaling in the maintenance of human embryonic stem celll pluripotency and viability highlighted by transcriptional profiling and functional analysis," Human Molecular Genetics 15:1460-2083,2006.

Arnold, "Brachyury is a target gene of the Wnt/beta-catenin signaling pathway," Mech. Dev., 91:249-258,2000.

Assady, et al., "Insulin production by human embryonic stem cells," Diabetes, 50:1691-7,2001.

Bachiller, et al., "The organizer factors chordin and noggin are required for mouse forebrain development," Nature, 403:658-661,2000.

Bain, et al., "Embryonic Stem Cells Express Neuronal Properties in Vitro," Dev Biol. 168:342-57,1995.

Barbacci, et al., "Variant Hepatocyte Nuclear Factor 1 Is Required for Visceral Endoderm Specification," Development 126:4795-4805,1999.

Barry, et al., "Production of monoclonal antibodies by genetic immunization," Biotechniques 16:616-620,1994.

Battle, et al., "The transcription factor snail is a repressor of E-cadherin gene expression in epithelial tumour cells," Nat. Cell. Biol., 2:84-89,2000.

Beck, et al., "Extra-embryonic proteases regulate Nodal signaling during gastrulation," Nat Cell Biol 4:981-985,2002.

Beddington, et al., "*Brachyury*—a gene affecting mouse gastrulation and easly organogenesis," Dev Suppl.:157-65,1992.

Bendall, et al., "IGF and FGF cooperatively establish regulatory stem cell niche of pluripotent human cells in vitro," Nature 448:1015-1021,2007.

Bongso, et al., "Isolation and culture of inner cell mass cells from human blastocysts," Hum Reprod. 9:2110-2117,1994.

Bost, et al., "Retinoic Acid Activation of the ERK Pathway is Required for Embryonic Stem Cell Commitment into the Adipocyte Lineage," Biochem J. 361(Pt 3):621-627,2002.

Brennan, et al., "Nodal signaling in the epiblast patterns the early mouse embryo," Nature,411:965-969,2001.

Candia, et al., "Differential localization of mox-1 and mox-2 proteins indicates distinct roles during development," Int. J. Dev. Biol. 40:1179-1184,1996.

Candia, et al., "Mox-1 and Mox-2 define a novel homebox gene subfamily and are differentially expressed during early mesodermal patterning in mouse embryos," Development ,116:783-797,1992.

Cereghini, et al., "Expression Patterns of vHNF1 and HNF1 Homeoproteins in Early Postimplantation Embryos Suggest Distinct and Sequential Developmental Roles," Development 116:783-797,1992.

Chang, et al., "Genetic analysis of the mammalian transforming growth factor-beta superfamily.," Endocr Rev. 23:787-823,2002.

Chen, et al., "Retinoic acid signaling is essential for pancreas development and promotes endocrine at the expense of exocrine cell differentiation in xenopus," Developmental Biology, 271:144-160,2004.

Chiruna, et al., "FGF signaling regulates mesoderm cell fate specification and morphogenetic movement at the primitive streak," Development, 124:2829-2841,1997.

Cocco, et al., "Synthesis, characterisation and insulin-mimetic activity of oxovanadium(IV) complexes with amidrazone derivatives," J Inorg Biochem. 101:19-29,2007.

Collombat, et al., "Specifying pancreatic endocrine cell fates," Mech. Dev. 123:501-12,2006.

Conley, et al., "Bmps Regulate Differentiation of a Putative Visceral Endoderm Layer Within Human Embryonic Stem-Cell-Derived Embryoid Bodies," Biochem Cell Biol 85:121-132,2007.

Conlon, et al., "A primary requirement for nodal in the formation and maintenance of the primitive streak in the mouse," Development. 120:1919-28,1994.

Costaglia, et al., "Genetic immunization against the human thyrotropin receptor causes thyroiditis and allows production of monoclonal antibodies recognizing the native receptor," J. Immunol 160:1458-1465,1998.

Czyz, et al., "Embryonic Stem Cell Differentiation: The Role of Extracellular Factors," Differentiation 68:167-174,2001.

D'Amour, et al., "Efficient differentiation of human embryonic stem cells to definitive endoderm," Nature Biotechnology vol. 23:1534-1541,2005.

D'Amour, et al., "Production of Pancreatic Hormone-Expressing Endocrine Cells From Human Embryonic Stem Cells ," Nature Biotechnology 24:1392-1401,2006.

Daheron, et al., "LIF/STAT3 Signaling Fails to Maintain Self-Renewal of Human Embryonic Stem Cells," Stem Cells 22:770-8,2004.

Dani, et al., "Differentiation of Embryonic Stem Cells into Adipocytes in Vitro," J Cell Sci. 110:1279-1285,1997.

De Caestecker, "The transforming growth factor-beta superfamily of receptors," Cytokine Growth Factor Rev 15:1-11,2004.

Defelice, et al., "TTF-1 Phosphorylation is required for peripheral lung Morphogenesis, Perinatal Survival, and Tissue-Specific Gene Expression," J Biol Chem. 278:35574-35583,2003.

Dougan, et al., "The role of the zebrafish nodal-related genes Squint and Cyclops in patterning of mesendodern," Development. 130:1837-51,2003.

Edlund, "Factors Controlling Pancreatic Cell Differentiation and Function," Diabetologia. 44:1071-9,2001.

Elms, et al., "Overlapping and Distinct Expression Domains of Zic2 and Zic3 during mouse gastrulation," Gene Expression Patterns 4:505-11, 2004.

Falasca, et al., "Retinoic Acid Treatment Induces Apoptosis or Expression of a More Differentiated Phenotype on Different Fractions of Cultured Fetal Rat Hepatocytes Hepatology," Hepatology. 28:727-37,1998.

Fehling, et al., Fehling et al., "Development and Disease: Tracking Mesoderm Induction and its Specification to the Hemangioblast during Embryonic Stem Cell Differentiation," Development. 130:4217-4227,2003.

Feldman, et al., "Zebrafish organizer development and germ-layer formation require nodal-related signals," Nature. 395:181-5,1998.

Feng, et al., "HIV-1 entry cofactor: functional cDNA cloning of a seven-transmembrance, G protein-coupled receptor," Science. 272:872-7,1996.

Freund, et al., "Insulin redirect differentiation from cardiogenic mesoderm and endoderm to neuroectoderm in differentiating human embryonic stem cells," Stem Cells, published online Dec. 20, 2007.

Futaki, et al., "Molecular basis of constitutive production of basement membrane components: Gene expression profiles of engelbreth-holm-swarm tumor and F9 embryonal carcinoma cells," J Biol. Chem. 278:50691-701,2003.

Goumans, et al., "Mouse Embryonic Stem Cells with Aberrant Transforming Growth Factor B signaling Exhibit Impaired Differentiation in Vitro and in Vivo," Differentiation. 63:103/113,1998.

Grapin-Botton, "Endoderm development: from patterning to organogenesis," Trends Genet. 16:124-30,2000.

Haegel, et al., "Lack of β-catenin Affects Mouse Development at Gastrulation," Development 121:3529-3537,1995.

Hallonet, et al., "Maintenance of the Specification of the Anterior Definitive Endoderm and Forebrain Depends on the Axial Mesendoderm: A Study Using HNF3R/Foxa2 Conditional Mutants," Dev Biol 243:20-33,2002.

Hamazaki, et al., "Hepatic Maturation in Differentiating Embryonic Stem Cells in Vitro," FEBS Lett. 497:15-9,2001.

Hansson, et al., "Artifactual Insulin Release from Differentiated Embryonic Stem Cells," Diabetes 53:2603-2609,2004.

Harris, et al., "Global gene expression patterns during differentiation of F9 embryonal carcinoma cells into parietal endoderm," Funct Integr Genomics. 2:105-19,2002.

Harrision, et al., "Pancreas Dorsal Lobe Agenesis and Abnormal Islets of Langerhans in HIxb9-deficient Mice," Nature Genetics 23:71-75,1999.

Haumaitre, et al., "Functions of HNF1 Family Members in Differentiation of the Visceral Endoderm Cell Lineage," J. Biol. Chem. 278:40933-40942,2003.

Henry, et al., "Mixer, a Homeobox Gene Required for Endoderm Development," Science 281:91-96,1998.

Herrmann, et al., "Cloning of the T Gene Required in Mesoderm Formation in the Mouse," Nature 343:617-622,1990.

Hogan, "Bone morphogenetic proteins in development," Curr Opin Genet Dev. 6:432-8,1996.

Holland, et al., "Experimental control of pancreatic development and maintenance," Proc Natl Acad Sci USA 99:236-241,2002.

Houard, et al., "HNF-6-Independent Differentiation of Mouse Embryonic Stem Cells into Insulin-Producing Cells," Diabetologia 46:378-385,2003.

Howe, et al., "Expression of SPARC/osteonectin transcript in murine embryos and gonads," Differentiation. 37:20-5,1988.

Hudson, et al., "Xsox17alpha and—beta mediate endoderm formation in Xenopus," Cell. 91:397-405,1997.

Huelsken, et al., "Requirement for β-Catenin in Anterior-Posterior Axis Formation in Mice," J Cell Biol 148:567-578,2000.

Humphrey, et al., "Maintenance of Pluripotency in Human Embryonic Stem Cells is STAT3 Independent," Stem Cells 22:522-30,2004.

Imada, et al., "Fetomodulin: Marker surface protein of fetal development which is modulatable by cyclic AMP," Dev Biol. 122:483-91,1987.

Jain, et al., "Glucose Control and Long-Term Survival in Breeding/Worcester Rats After Intraperitoneal Implantation of Hydrophilic Macrobeads containing Porcine Islets without Immunosuppression," Transplantation. 68:1693-700,1999.

Jones, et al., "Differences Between Human and Mouse Alpha-Fetoprotein Expression During Early Development," J. Anat. 198:555-9,2001.

Jonsson, et al., "Insulin-promoter-factor 1 is required for pancreas development n. mice," Nature, vol. 371:606-609,1994.

Kahan, et al., "Pancreatic Precursors and Differentiated Islet Cell Types from Murine Embryonic Stem Cells: An in Vitro Model to Study Islet Differentiation," Diabetes 52:2016-2024,2003.

Kalinchenko, et al., "The Forkhead Box F1 Transcription Factor is Expressed in Brain and Head Mesenchyme During Mouse Embryonic Development," Gene Expr Patterns 3:153-158,2003.

Kanai-Azuma, et al., "Depletion of definitive gut endoderm in Sox17-null mutant mice," Development. 129:2367-79,2002.

Katoh, "Expression of human SOX7 in normal tissues and tumors," Int J Mol Med. 9:363-8,2002.

Kawahira, et al., "Hedgehog Signaling Regulates Expansion of Pancreatic Epithelial Cells," Developmental Biology 280:111-121,2005.

Keller, "In vitro differentiation of embryonic stem cells," Curr Op Cell Biol 7:862-869,1995.

Kieffer, et al., "The Glucagon-Like Peptides," Endocr Rev. 20:876-913,1999.

Kikuchi, et al., "Casanova encodes a novel Sox-related protein necessary and sufficient for early endoderm formation in zebrafish," Genes Dev. 15:1493-1505,2001.

Kilpatrick, et al., "Gene gun delivered DNA-based immunizations mediate rapid production of murine monoclonal antibodies to the Flt-3 receptor," Hybridoma 17:569-576,1998.

Kim, et al., "Chemokines: signal lamps for trafficking of T and B cells for development and effector function," J Leukoc Biol. 65:6-15,1999.

Kim, et al., "Retracted: contribution of the PI3K/Akt/PKB signal pathway to maintenance of self-renewal in humen embryonic stem cells," FEBS Letters 579:534-40,2005.

Kimelman, et al., "Vertebrae mesenderm induction and patterning," Curr Opin Genet Dev. 10:350-6,2000.

Kinder, et al., "The Organizer of the Mouse Gastrula is Composed of a Dynamic Population of Progenitor Cells for the Axial Mesoderm," Development 128:3623-3634,2001.

Krasemann, et al., "Generation of monoclonal antibodies against proteins with an unconventional nucleic acid-based immunization strategy," J Biotechnol. 73:119-29.,1999.

Labosky, et al., "Embryonic germ cell lines and their derivation from mouse primordial germ cells," Ciba Found Symp. 182:157-68,discussion 168-78,1994.

Labosky, et al., "Mourse embryonic germ (EG) cell lines: transmission through the germline and differences in the methylation imprint of insulin-like growth factor 2 receptor (Igf2r) gene compared with embryonic stem (ES) cell lines," Development. 120:3197-204,1994.

Latif, et al., "A Simple Method of Staining Fresh and Cultured Islets," Transplantation 45:827-30,1998.

Lawson, et al., "Bmp4 is Required for the Generation of Primordial Germ Cells in the Mouse Embryo," Genes Dev 13:424-436,1999.

Li, et al., "MEK/ERK signaling contributes to the maintenance of human embryonic stem cell self-renewal," Differentiation,75:299-307,2007.

Li, et al., "Selective Agenesis of the Dorsal Pancreas in Mice Lacking Homeobox Gene HIxb9," Nature Genetics 23:67-70,1999.

Lickert, et al., "Formation of multiple hearts in mice following deletion of betacatenin in the embryonic endoderm," Dev Cell. 3:171-81,2002.

Liu, et al., "Requirement for Wnt3 in Vertebrate Axis Formation," Nat Genet 22:361-365,1999.

Lobel et al "A gut feeling," Nat. Biotechnol 23:1491-2,2005.

Lowe, et al., "Genetic dissection of nodal function in patterning the mouse embryo," Development,128:1831-1843,2001.

Lu, et al., "From fertilization to gastrulation: axis formation in the mouse embryo," Curr Opin Genet Dev. 11:384-92,2001.

Lumelsky, et al., "Differentiation of Embryonic Stem Cells to Insulin-Secreting Structures Similar to Pancreatic Islets," Science. 292:1389-94,2001.

Ma, et al., "The chemokine receptor CXCR4 is required for the retention of B lineage and granulocytic precursors within the bone marrow microenvironment," Immunity. 10:463-71,1999.

Martin, et al., "Dorsal Pancreas Agenesis in Retinoic Acid-Deficient Raldh2 Mutant Mice," Developmental Biology 284:399-411,2005.

Maruoka, et al., "Comparison of the Expression of Three Highly Related Genes, Fgf8, Fgf17 and Fgf18, in the Mouse Embryo," Mech Dev 74:175-177,1998.

Matsuda, et al., "STAT3 Activation is Sufficient to Maintain an Undifferentiated State of Mouse Embryonic Stem Cells," EMBO J 18:4261-9,1999.

McGrath, et al., "Expression of Homeobox Genes, Including and Insulin Promoting Factor, in the Murine Yolk Sac at the Time of Hematopoietic Initiation," Dev Biol. 213:442-56,1999.

McGrath, et al., "Embryonic expression and function of the chemokine SDF-1 and its receptor, CXCR4," Mol Reprod Dev 48:145-153,1997.

McLean, et al., "Activin a Efficiently Specifies Definitive Endoderm from Human Embryonic Stem Cells Only When Phosphtidylinositol 3-Kinase Signaling Is Suppressed," Stem Cells 25:29-38,2007.

Mendi, et al., "Involvement of insulin-like growth factor type 1 receptor and protein kinase Cdelta in bis(maltolato)oxovanadium(IV)-induced phosphorylation of protein kinase B in HepG2 cells," Biochemistry, 45:11605-15,2006.

Micallef, et al., "Retinoic Acid Induces Pdx1-positive Endoderm in Differentiating mouse embryonic stem cells," Diabetes 54:301-305,2005.

Millonig, et al., "Molecular Analysis of the Distal Enhancer of the Mouse Alpha-Fetoprotein Gene," Mol. Cell Biol. 15:3848-3856,1995.

Milne, et al., "Generation of Insulin-Expressing Cells from Mouse Embryonic Stem Cells," Biochemical and Biophysical Research Communications 328:399-403,2005.

Miyazono, et al., "Divergence and convergence of TGF-beta/BMP signaling.," J Cell Physiol. 187:265-76,2001.

Mizusawa, et al., "Differentiation Phenotypes of Pancreatic Islet Beta- and Alpha-Cells are Closely Related with Homeotic Genes and a Group of Defferentially Expressed Genes," Gene. 331:53-63,2004.

Molotkov, et al., "Retinoic Acid Generated by Raldh2 in Mesoderm Is Required for Mouse Dorsal Endodermal Pancreas Development," Development Dynamics 232:950-957,2005.

Moriya, et al., "In Vitro Pancreas Formation from Xenopus Ectoderm Treated with Activin and Retinoic Acid," Dev Growth Differ. 42:593-602,2000.

Nagai, et al., "The Expression of the Mouse Zic1, Zic2, and Zic3 Gene Suggests an Essential Role for Zic Genes in Body Pattern Formation," Dev Biol 182:299-313,1997.

Nagasawa, et al., "Defects of B-cell lymphopoiesis and bone-marrow myelopoiesis in mice lacking the CXC chemokine PBSF/SDF-1.," Nature. 382:635-8,1996.

Nakagawa, et al., "Recruitment and Activation of Rac1 by the Formation of E-cadherin-mediated Cell-cell Adhesion Sites," J. Cell Science 114:1829-1838,2001.

Nieto, "The Snail Superfamily of Zinc-Finger Transcription Factors," Nat Rev Mol Cell Biol 3:155-166,2002.

Niimi, et al., "SOX7 and SOX17 Regulate the Parietal Endoderm-Specific Enhancer Activity of Mouse Laminin Alpha1 Gene," J. Biol. Chem. 279:38055-38061,2004.

Niswander, et al., "Fgf-4 Expression During Gastrulation, Myogenesis, Limb and Tooth Development in the Mouse," Development 114:755-768,1992.

Niwa, "Molecular mechanism to maintain stem cell renewal of ES cells," Cell Struct Funct. 26:137-48,2001.

Offield, et al., "PDX-1 is Required for Pancreatic Outgrowth and Differentiation of the Rostral Duodenum," Development 122:983-995,1996.

Ogura, et al., "Behavioral abnormalities of Zic1 and Zic2 mutant mice: implications as models for human neurological disorders," Behav Genet. 31:317-24,2001.

O'Hare, et al., "Conditional Immortalization of Freshly Isolated Human Mammary Fibroblast and Endothelial Cells," Proc Natl Acad Sci U S A. 98:646-51,2001.

Ormestad, et al., "Differences in the Embryonic Expression Patterns of Mouse Foxf1 and -2 Match Their Distinct Mutant Phenotypes," Developmental Dynamics 229:328-333,2004.

Paling, et al., "Regulation of embryonic stem cell self-renewal by phosphoinositide 3-kinase dependent signaling," Journal of Biological Chemistry 279:48063-48070,2004.

Pearce, et al., "Mml, a Mouse Mix-like Gene Expressed in the Primitive Streak," Mech Dev 87:189-192,1999.

Pera, et al., "Regulation of Human Embryonic Stem Cell Differentiation by BMP-2 and its Antagonist Noggin," J Cell Sci 117:1269-1280,2004.

Perea-Gomez, et al., "Initiation of Gastrulation in the Mouse Embryo is Preceded by an Apparent Shift in the Orientation of the Anterior-Posterior Axis," Curr Biol 14:197-207,2004.

Pesce, et al., "Oct-4: Gatekeeper in the Beginnings of Mammalian Development," Stem Cells 19:271-278,2001.

Pevny, et al., "A Role for SOX1 in Neural Determination," Development 125:1967-1978,1998.

Phillips, et al., "Differentiation of Embryonic Stem Cells for Pharmacological Studies on Adipose Cells," Pharmacol Res. 47:263-8,2003.

Rajagopal, et al., "Insulin Staining of ES Cell Progeny from Insulin Uptake," Science 299:363,2003.

Rambhatla, et al., "Generation of hepatocyte-like cellls from human embryonic stem cells," Cell Transplantation12:1-11,2003.

Reubinoff, et al., "Embryonic stem cell lines from human blastocysts: somatic differentiation in vitro," Nat Biotechnol. 18:399-404,2000.

Robb, et al., "Gastrula Organiser and Embryonic Patterning in the Mouse," Seminars in Cell & Dev. Biol 15:543-554,2004.

Roche, et al., "Ectodermal commitment of insulin-producing cells derived from mouse embryonic stem cells," Faseb J 19:1341-3,2005.

Rodaway, et al., "Induction of the mesendoderm in the zebrafish germ ring by yolk cell-derived TGF-beta family signals and discrimination of mesoderm and endoderm by FGF," Development. 126:3067-78,1999.

Rodaway, "Mesendoderm, an ancient germ layer?," Cell. 105:169-72,2001.

Rohr, et al., "Zebrafish zic1 expression in brain and somites is affected by BMP and hedgehog signaling," Mech Dev. 85:147-59,1999.

Rossant, et al., "Emerging Asymmetry and Embryonic Patterning in Early Mouse Development," Dev Cell 7:155-164,2004.

Sakurai, et al., "The pharmacology of the insulinomimetic effect of zinc complexes," Biometals 18:319-23,2005.

Sander, et al., "The Beta Cell Transcription Factors and Development of the Pancreas," J Mol Med. 75:327-40,1997.

Sasaki, et al., "Differential expression of multiple fork head related genes during gastrulation and axial pattern formation in the mouse embryo," Development 118:47-59,1993.

Schier, "Nodal signaling in vertebrate development," Annu Rev Cell Dev Biol. 19:589-621,2003.

Schmolke, et al., "Identification of hepatitis G virus particles in human serum by E2-specific monoclonal antibodies generated by DNA immunization," J Virol. 72:4541-45,1998.

Schoenwolf, et al., "Gastrulation and early mesodermal patterning in vertebrates," Methods Mol Biol 135:113-125,2000.

Schuldiner, et al., "Effects of Eight Growth Factors on the Differentiation of Cell Derived from Human Embryonic Stem Cells," Proc Natl Acad Sci U S A. 97:11307-12,2000.

Segev, et al., "Differentiation of human embryonic stem cells into insulin-producing clusters," Stem Cells 22:265-274,2004.

Shalaby, et al., "Failure of Blood-Island Formation and Vasculogenesis in Flk1-deficient Mice," Nature 376:62-66,1995.

Shamblott, et al., "Derivation of pluripotent stem cells from cultured human primordial germ cells," Proc Natl Acad Sci U S A. 95:13726-31,1998.

Shapiro, et al., "Could fewer islet cells be transplanted in type 1 diabetes? Insulin independence should be dominant force in islet transplantation," BMJ. 322:861,2001.

Shapiro, et al., "Islet transplantation in seven patients with type 1 diabetes mellitus using a glucocorticoid-free immunosuppressive regimen," N Engl J Med. 343:230-8,2000.

Shapiro, et al., "Pancreatic islet transplantation in the treatment of diabetes mellitus," Best Pract Res Clin Endocrinol Metab. 15:241-64,2001.

Shi, et al., "Inducing embryonic stem cells to differentiate into pancreatic beta cells by a novel three-step approach with activin A and all-trans retinoic acid," Stem Cells 23:656-662,2005.

Shiozawa, et al., "Cloning and characterization of Xenopus laevis xSox 7 xDNA," Biochim Biophys Acta. 1309:73-6,1996.

Shiraki, et al., "TGF-beta signaling potentiates differentiation of embryonic stem cells to PDx-1 expressing endodermal cells," Genes to Cells 21:405-412,2005.

Shook, et al., "Mechanisms, Mechanics and Function of Epithelial-Mesenchymal Transitions in Early Development," Mech Dev 120:1351-1383,2003.

Sinner, et al., "Sox17 and β-Catenin Cooperate to Regulate the Transcription of Endodermal Genes," Development 131:3069-3080,2004.

Skoudy, et al., "Transforming Growth Factor (TGF) beta, Fibroblast Growth Factor (FGF) and Retinoid Signaling Pathways Promote Pancreatic Exocrine Gene Expression in Mouse Embryonic Stem Cells.," Biochem J. 379:749-756,2004.

Smith, et al., "Brachyury and the T-box genes," Curr Opin Genet Dev. 7:474-80,1997.

Smith, et al., "Upstream and downstream from Brachyury, a gene required for vertebrae mesoderm formation," Cold Spring Harb Symp Quant Biol. 62:337-46,1997.

Sooknanan, et al., "NASBA: a detection and amplification system uniquely suited for RNA," Nature Biotechnology 13:563-564,1995.

Soon-Shiong, "Treatment of Type I Diabetes using Encapsulated Islets," Adv Drug Deliv Rev. 35:259-270,1999.

Soria, et al., "Insulin-Secreting Cells Derived from Embryonic Stem Cells Normalize Glycemia in Streptozotocin-Induced Diabetic Mice," Diabetes. 49:157-62,2000.

Stafford, et al., "A Conserved Role for Retoid Signaling in Verterbrate Pancreas Development.," Dev Genes Evol. 214:432-441,2004.

Stafford, et al., "Retioic Acid Signaling Is Required for a Critical Early Step in Zebrafish Pancreatic Development," Curr Biol. 12:1215-20,2002.

Stafford, et al., "The Role of Retinoid Signaling in Pancreas Differentiation," Pancreatic Development, Proliferation and Stem Cells, Meeting Abstract October, National Institute of Health.:,2001.

Stainier, "A Glimpse into the Molecular Entrails of Endoderm Formation," Genes Dev 16:893-907,2002.

Stemmler, et al., "Analysis of Regulatory Elements of E-Cadherin with Reporter Gene Constructs in Transgenic Mouse Embryos," Developmental Dynamics 227:238-245,2003.

Stoffers, et al., "Pancreatic Agenesis Attributable to a Single Nucleotide Deletion in the Human IPF1 Gene Coding Sequence," Nature Genetics 15:106-110,1997.

Suzuki, et al., "Cloned Cells Develop Renal Cortical Collecting Tubles," Nephron. 68:118-24,1994.

Tada, et al., "Characterization of Mesendoderm: A Diverging Point of the Definitive Endoderm and Mesoderm in Embryonic Stem Cell Differentiation Culture," Development 132:4363-4374,2005.

Takash, et al., "SOX7 transcription factor: sequence, chromosomal localization, expression, transactivation and interference with Wnt signaling," Nucleic Acids Res. 29:4274-83,2001.

Tam, et al., "Early endoderm development in vertebrate: lineage differentiation and morphogenetic function," Curr. Opin. Genet. Dev. 13:393-400,2003.

Tam, et al., "Gene function in mouse embryogenesis: get set for gastrulation," Nat. Rev. Genet. 8:368-81,2007.

Taniguchi, et al., "Isolation and characterization of a mouse SRY-related cDNA, mSox7," Biochim Biophys Acta. 1445:225-31,1999.

Technau, "Brachyury, the blastopore and the evolution of the mesoderm," Bioessays. 23:788-94,2001.

Thomas, et al., "The Murine Gene, Traube, Is Essential for the Growth of Preimplantation Embryos," Dev Biol 227:324-342,2000.

Thomson, et al., "Embryonic stem cell lines derived from human blastocysts," Science. 282:1145-7,1998.

Tiedemann, et al., "Pluripotent cells (stem cells) and Their Determination and Differentiation in Early Vertebrate Embryogenesis," Dev Growth Differ. 43:469-502,2001.

Tremblay, et al., "Formation of the definitive endoderm in mouse is a Smad2-dependent process," Development. 127:3079-90,2000.

Tutter, et al., "Embryonic Stem Cells: A great new hope for a new era of medicine," Development 127:3079-3090,2000.

Ulivieri, et al., "Generation of a monoclonal antibody to a defined portion of the Heliobacter pylori vacuolating cytotoxin by DNA immunization," J Biotechnol. 51:191-4,1996.

Urbach, et al., "Modeling Lesch-Nyhan Disease by Gene Targeting in Human Embryonic Stem Cells," Stem Cells 22:635-641,2004.

Vallier, et al., "Activin/Nodal and FGF Pathways Cooperate to Maintain Pluripotency of Human Embryonic Stem Cells," J Cell Sci. 118:4495-509,2005.

Vallier, et al., "Nodal Inhibits Differentiation of Human Embryonic Stem Cells Along the Neuroectodermal Default Pathway," Developmental Biology 275:403-421,2004.

Vandesompele, et al., "Accurate normalization of real-time quantitative RT-PCR data by geometric averaging of multiple internal control genes," Genome Biol. 3:2002,2002.

Varlet, et al., "Nodal expression in the primitive endoderm is required for specification of the anterior axis during mouse gastrulation," Development. 124:1033-44,1997.

Vincent, et al., "Cell fate decisions within the mouse organizer are governed by graded nodal signals," Genes Dev. 17:1646-62,2003.

Vogel, "Stem Cells are Coaxed to Produce Insulin," Science. 292:615-616,2001.

Wang, et al., "Self-renewal of human embryonic stem cells requires insulin-like growth factor-1 receptor and ERBB2 receptor signaling," Blood 10:4110-4119,2007.

Wei, et al., "Transcriptome Profiling of Human and Murine ESCs Identifies Divergent Paths Required to Maintain the Stem Cell State," Stem Cells 23:166-185,2005.

Weiler-Guettler, et al., "Developmentally regulated gene expression of thrombomodulin in postimplantation mouse embryos," Development. 122:2271-81,1996.

Weiler-Guettler, et al., "Thrombomodulatin gene regulation by cAMP and retinoic acid in F9 embryonal carcinoma cells," PNAS 89:2155-9,1992.

Weinstein, et al., "The winged-helix transcription factor HNF-3 beta is required for notochord development in the mouse embryo," Cell 78:575-588,1994.

Wells, et al., "Early mouse endoderm is patterned by soluble factors from adjacent germ layers," Development. 127:1563-72,2000.

Wells, et al., "Vertebrate endoderm development," Annu Rev Cell Dev Biol.:393-410,1999.

Wilding, et al., "The role of pdx1 and HNF6 in proliferation and differentiation of endorine precursors," Diabetes Metab Res Rev. 20:114-23,2005.

Willison, "The mouse Brachyury gene and mesoderm formation.," Trends Genet. 6:104-5,1990.

Xu, et al., "BMP4 initiates human embryonic stem cell differentiation to trophoblast," Nature Biotechnology 20:1261-1264,2002.

Xu, et al., "Characterization and Enrichment of Cardiomyocytes Derived From Human Embryonic Stem Cells," Circ Res. 91:501-8,2002.

Yamaguchi, et al., "flk-1, an flt-related Receptor Tyrosine Kinase is an Early Marker for Endothelial Cell Precursors," Development 118:489-498,1993.

Yamaguchi, et al., "T (Brachyury) is a Direct Target of Wnt3a During Paraxial Mesoderm Specification," Genes Dev 13:3185-3190,1999.

Yang, et al., "Disabled-2 is Essential for Endodermal Cell Positioning and Structure Formation During Mouse Embryogenesis," Dev Biol 251:27-44,2002.

Yasunaga, et al., "Induction and Monitoring of Definitive and Visceral Endoderm Differentiation of Mouse ES Cells," Nat Biotechnol 23:1542-1550,2005.

Ying, et al., "BMP induction of Id proteins suppresses differentiation and sustains embryonic stem cell self-renewal in collaboration with STAT3," Cell 115:281-292,2003.

Yusuf, et al., "Expression of chemokine receptor CXCR4 during chick embryo development," Anat. Embryol (Berl) 210:35-41,2005.

Zhao, "Consequences of knocking out BMP signaling in the mouse," Genesis. 35:43-56,2003.

Zhou, et al., "Nodal is a novel TGF-beta-like gene expressed in the mouse node during gastrulation," Nature. 361:543-7,1993.

Zwaka, et al., "Homologous Recombination in Human Embryonic Stem Cells," Nature Biotechnology vol. 21:319-21,2003.

* cited by examiner

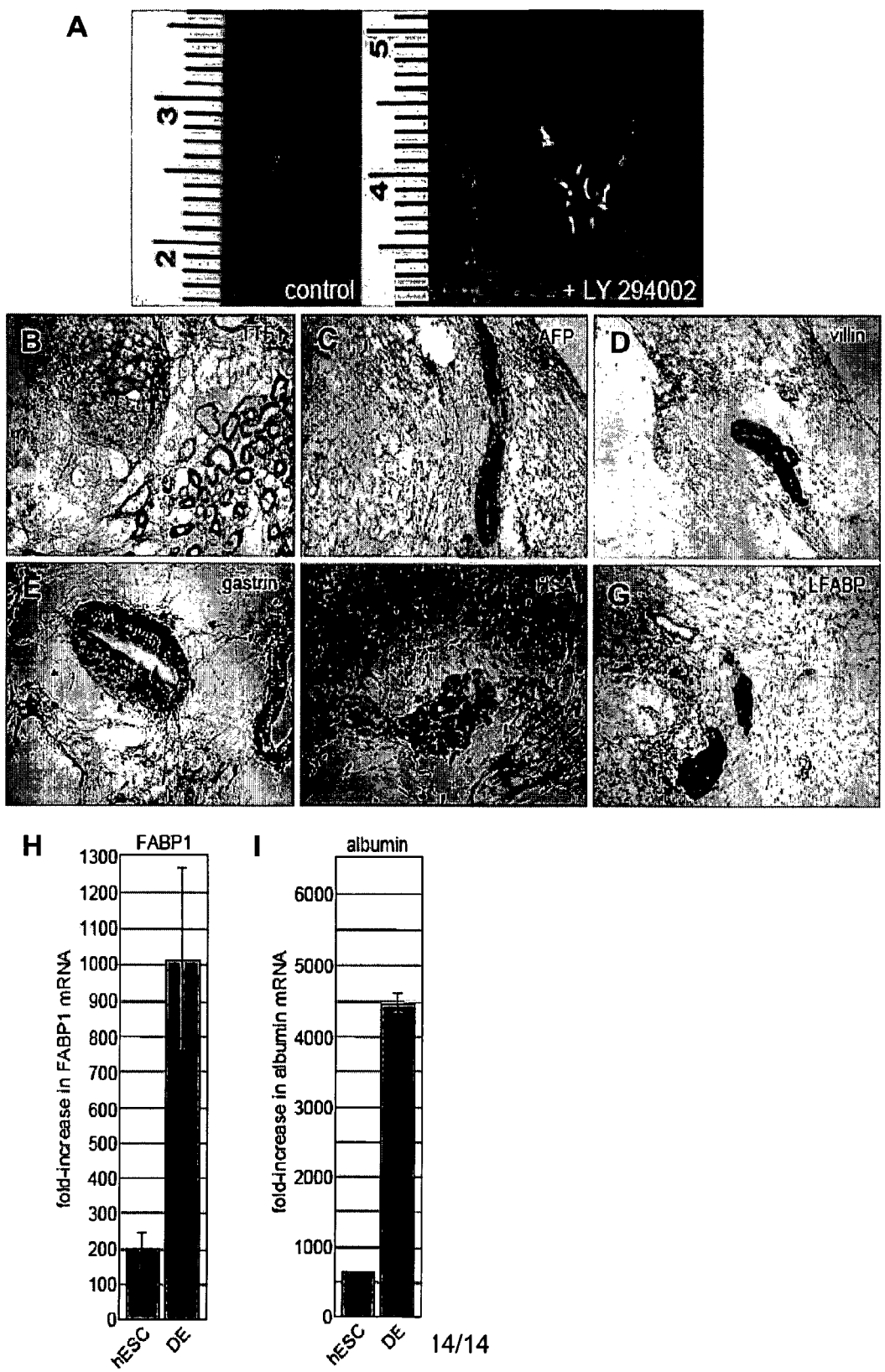

METHODS FOR INCREASING DEFINITIVE ENDODERM DIFFERENTIATION OF PLURIPOTENT HUMAN EMBRYONIC STEM CELLS WITH PI-3 KINASE INHIBITORS

Cross Reference to Related Applications

This application claims the priority benefit of PCT/US2005/028829 filed on Aug. 15, 2005 and U.S. Provisional Application Ser. No. 60/601,664 filed on Aug. 13, 2004, the entire contents of which are hereby incorporated by reference.

BACKGROUND OF THE INVENTION

1. Field of the Invention

The present invention generally relates to compositions and methods for differentiating and culturing pluripotent stem cells, the cells created by these methods and their uses thereof.

2. Background Art

Embryonic Stem (ES) cells represent a powerful model system for the investigation of mechanisms underlying pluripotent cell biology and differentiation within the early embryo, as well as providing opportunities for genetic manipulation of mammals and resultant commercial, medical and agricultural applications. Furthermore, appropriate proliferation and differentiation of ES cells can be used to generate an unlimited source of cells suited to transplantation for treatment of diseases that result from cell damage or dysfunction. Other pluripotent cells and cell lines including early primitive ectoderm-like (EPL) cells as described in International Patent Application WO 99/53021, in vivo or in vitro derived ICM/epiblast, in vivo or in vitro derived primitive ectoderm, primordial germ cells (EG cells), teratocarcinoma cells (EC cells), and pluripotent cells derived by dedifferentiation or by nuclear transfer will share some or all of these properties and applications.

The successful isolation, long-term clonal maintenance, genetic manipulation and germ-line transmission of pluripotent cells has generally been difficult and the reasons for this are unknown. International Patent Application WO 97/32033 and U.S. Pat. No. 5,453,357 describe pluripotent cells including cells from species other than rodents. Human ES cells have been described in International Patent Application WO 00/27995, and in U.S. Pat. No. 6,200,806, and human EG cells have been described in International Patent Application WO 98/43679.

The ability to tightly control differentiation or form homogeneous populations of partially differentiated or terminally differentiated cells by differentiation in vitro of pluripotent cells has proved problematic. Current approaches can involve the formation of embryoid bodies from pluripotent cells in a manner that is not controlled and does not result in homogeneous populations. Mixed cell populations such as those in embryoid bodies of this type are generally unlikely to be suitable for therapeutic or commercial use.

The biochemical mechanisms regulating ES cell pluripotency and differentiation are very poorly understood. However, the limited empirical data available (and much anecdotal evidence) suggests that the continued maintenance of pluripotent ES cells under in vitro culture conditions is dependent upon the presence of cytokines and growth factors present in the extracellular serum milieu. A number of such factors such as insulin, IGF(s) and FGF(s) have been found to activate intracellular signaling events through the lipid kinase phosphatidylinositol 3-kinase (PI3-kinase) (Carpenter & Cantley, (1996) Curr. Opin. Cell. Biol., 8: 153-158). In response to the binding of these soluble factors to specific cell surface receptors, PI3-kinase is recruited to the intracellular membrane surface where it initiates a cascade of secondary signaling events leading to the functional regulation of several downstream intracellular targets that influence diverse biological processes. Amongst the downstream targets of PI3-kinase is the protein kinase called 'mammalian Target Of Rapamycin' (mTOR). Stimulation of mTOR both precedes and is necessary for activation of ribosomal p70 S6 kinase, a serine/threonine kinase that is pivotal to the regulation of the protein synthetic machinery (Chung et al., (1994) Nature, 370: 71-75).

There is a need, therefore, to identify methods and compositions for the production of a population of cells enriched in a cell lineage through the manipulation of the PI3-kinase signaling pathway, the maintenance or stabilization, and proliferation of these cells, and the products of their further differentiation.

SUMMARY OF THE INVENTION

It is an object of the present invention to overcome, or at least alleviate, one or more of the difficulties or deficiencies associated with the prior art. One embodiment of the present invention relates to novel, defined processes for the production of definitive endoderm cells in culture using pluripotent cells. These processes provide the basis for efficient production of endodermal derived tissues such as pancreas, liver, lung, stomach, intestine and thyroid.

The present invention contemplates a composition comprising a population of isolated differentiated mammalian cells, wherein the cells are differentiated from a pluripotent cell in vitro, and wherein greater than approximately 50% of the cells express SOX17 but do not express AFP. In one embodiment of the invention, greater than approximately 60%, 65%, 70%, 75%, 80%, 85%, 90%, 91%, 92%, 93%, 94%, 95%, 96%, 97%, 98%, or 99% of the cells express SOX17 but do not express AFP.

The invention further contemplates a composition comprising a homogenous population of isolated definitive endoderm cells, wherein the cells were differentiated in an in vitro culture, and wherein greater than approximately 50% of the population are definitive endoderm cells. In certain embodiments, greater than approximately 60%, 65%, 70%, 75%, 80%, 85%, 90%, 91%, 92%, 93%, 94%, 95%, 96%, 97%, 98%, or 99% of the population are definitive endoderm cells. In one embodiment, the definitive endoderm cells express SOX17 but do not express AFP.

In an additional embodiment of the invention, the population has increased expression of HNF4alpha, GATA4, Mix1, and Msx1, and decreased expression of AFP in comparison to a population of spontaneously differentiating pluripotent cells. In a further embodiment, the population has increased expression of goosecoid, Brachyury, and Cerebrus, and decreased expression of AFP in comparison to a population of spontaneously differentiating pluripotent cells. It is also contemplated that the population can have increased expression of MIX1, goosecoid, and Cerebrus, and decreased expression of AFP in comparison to a population of spontaneously differentiating pluripotent cells. In one embodiment, the population does not have increased expression of SOX1 in comparison to a population of spontaneously differentiating pluripotent cells. In another embodiment, the population does not have increased expression of SOX7 in comparison to a population of spontaneously differentiating pluripotent cells. In another embodiment, the cells display similarly low expression of thrombomodulin as seen in a population of pluripotent cells as determined, for example, by flow cytometry.

The invention further encompasses a method of differentiating a pluripotent mammalian cell comprising: (a) providing the pluripotent mammalian cell, and (b) contacting the pluripotent mammalian cell with an effective amount of an inhibitor of the PI3-kinase signaling pathway and a member of the TGFβ family to at least partially differentiate the pluripotent cell to a cell of the endoderm lineage. In one embodiment, the member of the TGFβ family is selected from the group consisting of Nodal, Activin A, Activin B, TGF-β, BMP2, BMP4, and mixtures of the foregoing. In certain embodiments, the member of the TGFβ family is Activin A. It is contemplated that the member of the TGFβ can be exogenously added to the pluripotent mammalian cell in a substantially pure form, or can be present in a conditioned medium, as a substance produced by the feeder layer.

In one embodiment, the differentiated cell is isolated after step (b).

It is contemplated that the pluripotent cells have been differentiated by contact with a PI3-kinase inhibitor and a member of the TGFβ family.

In one embodiment, the cells are dissociated to an essentially single cell culture prior to being contacted with the inhibitor and the member of the TGFβ family. The cells can be dissociated using a protease, such as, but not limited to, trypsin.

In one embodiment, the cells are contacted with the PI3-kinase inhibitor and the member of the TGFβ family after being plated for between approximately 12 hours to approximately 6 days, after being plated for between approximately 12 hours to approximately 48 hours, or after being plated for approximately 24 hours. In certain embodiments, the pluripotent cells are plated at a concentration of less than approximately $2.5 \times 10^4$ cells/35 mm dish, of at least approximately $2.5 \times 10^4$ cells/35 mm dish, between approximately $2.5 \times 10^4$ to approximately $2 \times 10^5$ cells/35 mm dish, between approximately $5 \times 10^4$ to approximately $2 \times 10^5$ cells/35 mm dish, of less than approximately $4 \times 10^5$ cells/35 mm dish, or at a density of greater than $4 \times 10^5$ cells/35 mm dish.

In one embodiment, the cells are contacted with the PI3-kinase inhibitor and the member of the TGFβ family for greater than approximately 24 hours, for greater than approximately 48 hours, for greater than approximately 72 hours, or for approximately 72 hours. It is preferred that a composition comprising the inhibitor of the PI3-kinase pathway and the member of the TGFβ family is effective in causing differentiation of a pluripotent mammalian cell towards an endodermal lineage after the cell has been cultured with the composition for greater than approximately 24 hours. It is also contemplated that a composition comprising the inhibitor of the PI3-kinase pathway and the member of the TGFβ family is effective in causing differentiation of a pluripotent mammalian cell towards an endodermal lineage when the cell has been plated for greater than approximately 12 hours before it is contacted with the composition, or when the cell has been plated for approximately 24 hours before it is contacted with the composition.

The present invention further encompasses a composition for culturing cells, comprising a cell culture medium, an inhibitor of the PI3-kinase pathway, and a member of the TGFβ family. In certain embodiments of the foregoing, the inhibitor is selected from the group consisting of LY 294002, Rapamycin, wortmannin, lithium chloride, Akt inhibitor I, Akt inhibitor II, Akt inhibitor III, NL-71-101, and mixtures of the foregoing. In one embodiment, the inhibitor is Rapamycin. In certain embodiments, Rapamycin is initially present at a concentration of approximately 0.1 nM to approximately 500 nM, approximately 0.5 nM to approximately 250 nM, approximately 1.0 nM to approximately 150 nM, or approximately 1.5 nM to approximately 30 nM. In another embodiment, the inhibitor is LY 294002. In certain embodiments, LY 294002 is initially present at a concentration of approximately 1 µM to approximately 500 µM, approximately 2.5 µM to approximately 400 µM, approximately 5 µM to approximately 250 µM, approximately 10 µM to approximately 200 µM or approximately 20 µM to approximately 163 µM. In another embodiment, the inhibitor is AktI-II. In certain embodiments, AktI-II is initially present at a concentration of approximately 0.1 µM to approximately 500 µM, approximately 1 µM to approximately 250 µM, approximately 5 µM to approximately 20 µM, approximately 10 µM to approximately 100 µM or approximately 40 µM.

In a further embodiment, contacting the pluripotent cell with the inhibitor of the PI3-kinase pathway activates GSK3.

BRIEF DESCRIPTION OF THE DRAWINGS

FIG. 5A shows relative SOX17 gene expression; FIG. 5B shows relative Mix 1 gene expression; FIG. 5C shows relative goosecoid (GSC) gene expression; FIG. 5D shows relative GATA4 expression; FIG. 5E shows relative Cerebrus expression; FIG. 5F shows relative nodal gene expression; FIG. 5A shows relative Brachyury gene expression.

FIGS. 7A and K show relative AFP expression.

FIG. 12A shows a control kidney that does not contain an implant (left) and a kidney that contains an implant of hESCs treated for 4 days with 60 βM LY 294002 (right). The implant was grown under the kidney capsule of 5-week-old male SCID-beige mice for 6 weeks. The LY 294002 treated HESCs formed a large mass on the kidney. FIGS. 12B-G show photomicrographs of immunostainings of LY 294002 treated aggregates after culture under a kidney capsule for approximately 6 weeks. The aggregates express TTF-1 (B), AFP (C), villin (D), gastrin (E), HSA (F) and LFABP (G), indicating that the LY 294002 treated cells differentiate to derivatives of endoderm. FIGS. 12H and 12I demonstrate Q-PCR data showing a 1000-fold increase in FABP1 mRNA and a 4500-fold increase in albumin mRNA in LY294002 treated HESCs relative to LY 294002 treated cells that were not implanted. Assays were performed in triplicate and are shown as +/−SEM.

DETAILED DESCRIPTION OF THE INVENTION

Figure 1:
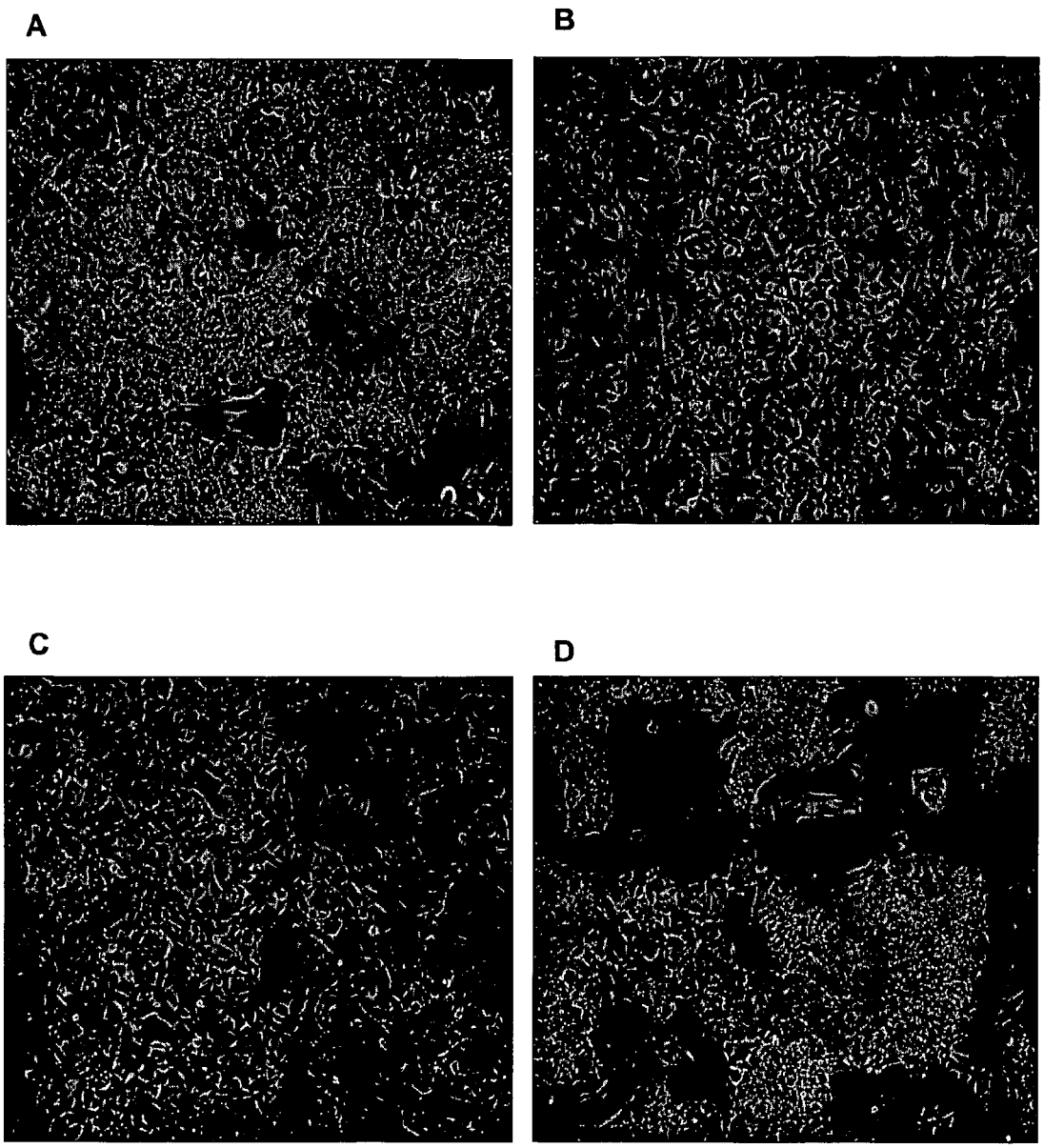
FIGS. 1A-D are photomicrographs at 10× magnification, showing the morphology of the human BG01 cell line. (A) shows untreated BG01 cells, (B) shows BG01 cells treated with 80 µM LY 294002, (C) shows BG01 cells treated with 30 nM rapamycin; and (D) shows the spontaneous differentiation of BG01 cells.
Figure 2:
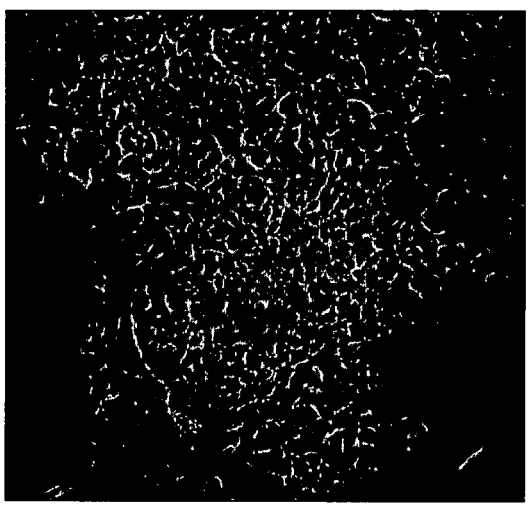
FIGS. 2A-D are photomicrographs at 20× magnification, showing the morphology of the human BG01 cell line. (A) shows untreated BG01 cells, (B) shows BG01 cells treated with 80 µM LY 294002, (C) shows BG01 cells treated with 30 nM rapamycin; and (D) shows the spontaneous differentiation of BG01 cells.
Figure 2:
Figure 2:
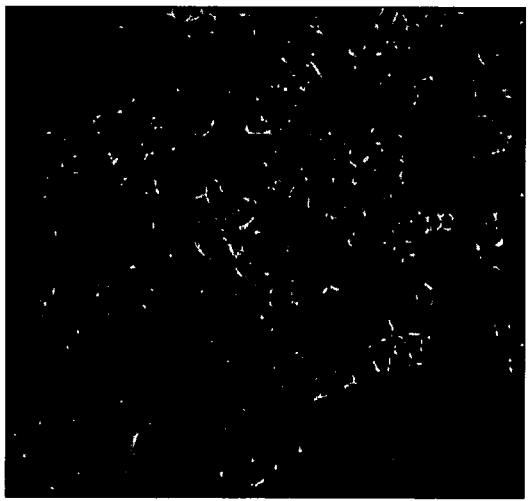
Figure 2:
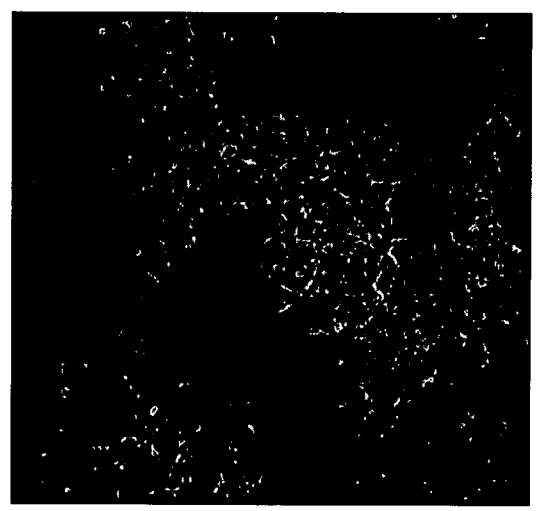
Figure 3:
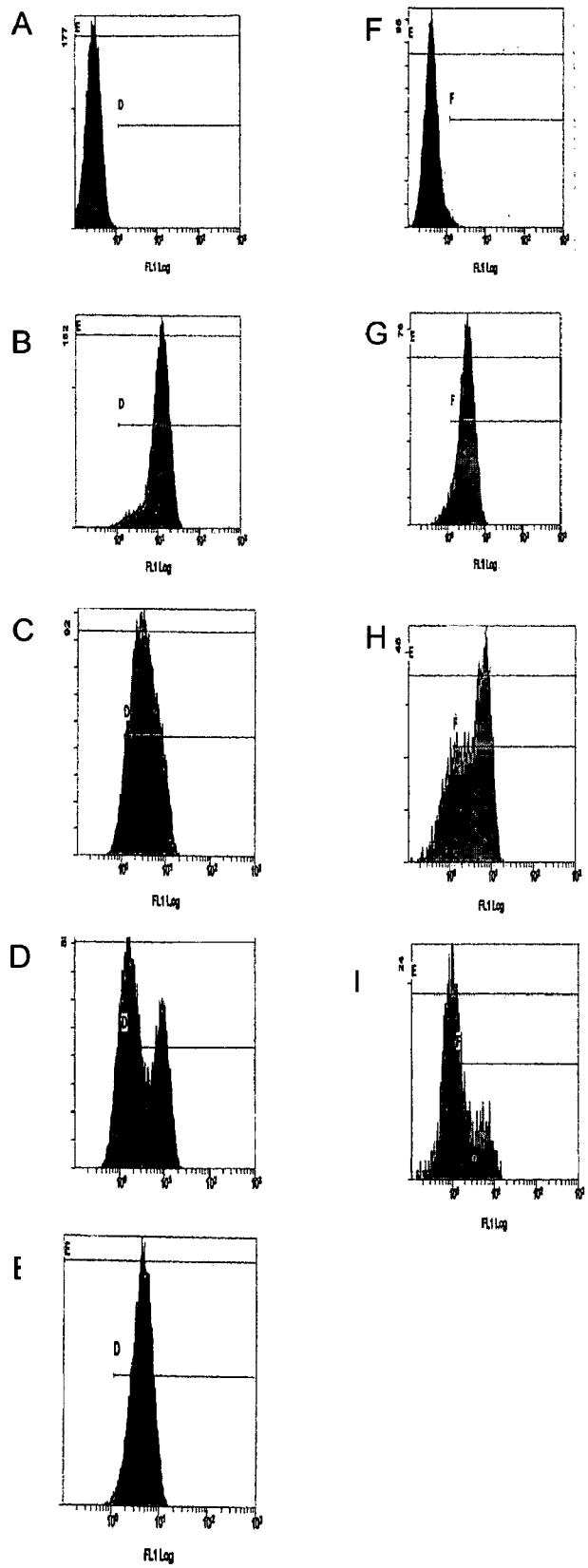
FIGS. 3A-E show the flow cytometry analysis of CD9 expression in human BG01 cells. (A) shows the secondary antibody alone, (B) shows untreated cells, (C) shows cells treated with 80 µM LY 294002, (D) shows cells treated with 30 nM rapamycin, and (E) shows spontaneously differentiated cells.
FIG. 3F-I show flow cytometry analysis of CD9 expression during embryoid body differentiation. (F) shows the secondary antibody alone, (G) shows undifferentiated BG01 cells, (H) shows embryoid bodies at day 3, and (I) shows embryoid bodies at day 5.

Applicant has demonstrated that culturing pluripotent mammalian cells with an inhibitor of PI3-kinase and a member of the TGFβ family generates differentiated cells wherein the cells have greater homogeneity than spontaneously differentiated cells.

The present invention contemplates a composition comprising a population of isolated differentiated mammalian cells, wherein the cells are differentiated from a pluripotent cell in vitro, and wherein greater than approximately 50% of the cells express SOX17 but do not express AFP. In one embodiment of the invention, greater than approximately 60%, 65%, 70%, 75%, 80%, 85%, 90%, 91%, 92%, 93%, 94%, 95%, 96%, 97%, 98%, or 99% of the cells express SOX17 but do not express AFP.

The invention further contemplates a composition comprising a homogenous population of isolated definitive endoderm cells, wherein the cells were differentiated in an in vitro culture, and wherein greater than approximately 50% of the population are definitive endoderm cells. In certain embodiments, greater than approximately 60%, 65%, 70%, 75%, 80%, 85%, 90%, 91%, 92%, 93%, 94%, 95%, 96%, 97%, 98%, or 99% of the population are definitive endoderm cells. In one embodiment, the definitive endoderm cells express SOX17 but do not express AFP.

In an additional embodiment of the invention, the population has increased expression of HNF4alpha, GATA4, Mix1, and Msx1, and decreased expression of AFP in comparison to a population of spontaneously differentiating pluripotent cells. In a further embodiment, the population has increased expression of Goosecoid, Brachyury, and Cerebrus, and decreased expression of AFP in comparison to a population of spontaneously differentiating pluripotent cells. It is also contemplated that the population can have increased expression of MIX1, Goosecoid, and Cerebrus, and decreased expression of AFP in comparison to a population of spontaneously differentiating pluripotent cells. In one embodiment, the population does not have increased expression of SOX1 in comparison to a population of spontaneously differentiating pluripotent cells. In another embodiment, the population does not have increased expression of SOX7 in comparison to a population of spontaneously differentiating pluripotent cells. In another embodiment, the cells display similarly low expression of thrombomodulin as seen in a population of pluripotent cells as determined, for example, by flow cytometry.

The invention further encompasses a method of differentiating a pluripotent mammalian cell comprising: (a) providing the pluripotent mammalian cell, and (b) contacting the pluripotent mammalian cell with an effective amount of an inhibitor of the PI3-kinase signaling pathway and a member of the TGFβ family to at least partially differentiate the pluripotent cell to a cell of the endoderm lineage. In one embodiment, the differentiated cell is isolated after step (b).

It is contemplated that the pluripotent cells have been differentiated by contact with a composition comprising a PI3-kinase inhibitor and a member of the TGFβ family. In one embodiment, the cells are dissociated to an essentially single cell culture prior to being contacted with the composition. The cells can be dissociated using a protease, such as, but not limited to, trypsin. The PI3-kinase inhibitor and the member of the TGFβ family do not need to be added simultaneously to the cell or cell culture, however, it is contemplated that during a point in culture, both the PI3-kinase inhibitor and the member of the TGFβ family will both be present in the composition.

In one embodiment, the cells are contacted with the composition after being plated for between approximately 12 hours to approximately 6 days, after being plated for between approximately 12 hours to approximately 48 hours, or after being plated for approximately 24 hours. In one embodiment, the cells are contacted with the composition for greater than approximately 24 hours, for greater than approximately 48 hours, for greater than approximately 72 hours, or for approximately 72 hours. It is preferred that the composition is effective in causing differentiation of a pluripotent mammalian cell towards an endodermal lineage after the cell has been cultured with the composition for greater than approximately 24 hours. It is also contemplated that the composition is effective in causing differentiation of a pluripotent mammalian cell towards an endodermal lineage when the cell has been plated for greater than approximately 12 hours before it is contacted with the composition, or when the cell has been plated for approximately 24 hours before it is contacted with the composition.

In certain embodiments, the pluripotent cells are plated at a concentration of less than approximately $2.5 \times 10^4$ cells/35 mm dish, of at least approximately $2.5 \times 10^4$ cells/35 mm dish, between approximately $2.5 \times 10^4$ to approximately $2 \times 10^5$ cells/35 mm dish, between approximately $5 \times 10^4$ to approximately $2 \times 10^5$ cells/35 mm dish, of less than approximately $4 \times 10^5$ cells/35 mm dish, or at a density of greater than $4 \times 10^5$ cells/35 mm dish.

The present invention further encompasses a composition for culturing cells, comprising a cell culture medium, an inhibitor of the PI3-kinase pathway, and a member of the TGFβ family. It is contemplated that the member of the TGFβ can be exogenously added to the pluripotent mammalian cell in a substantially pure form, or can be present in a conditioned medium, as a substance produced by the feeder layer.

In certain embodiments of the invention, the inhibitor is selected from the group consisting of LY 294002, Rapamycin, wortmannin, lithium chloride, Akt inhibitor I, Akt inhibitor II, Akt inhibitor III, NL-71-101, and mixtures of the foregoing. In one embodiment, the inhibitor is Rapamycin. In certain embodiments, Rapamycin is initially present at a concentration of approximately 0.1 nM to approximately 500 nM, approximately 0.5 nM to approximately 250 nM, approximately 1.0 nM to approximately 150 nM, or approximately 1.5 nM to approximately 30 nM. In another embodiment, the inhibitor is LY 294002. In certain embodiments, LY 294002 is initially present at a concentration of approximately 1 μM to approximately 500 μM, approximately 2.5 μM to approximately 400 μM, approximately 5 μM to approximately 250 μM, approximately 10 μM to approximately 200 μM or approximately 20 μM to approximately 163 μM. In another embodiment, the inhibitor is AktI-II. In certain embodiments, AktI-II is initially present at a concentration of approximately 0.1 μM to approximately 500 μM, approximately 1 μM to approximately 250 μM, approximately 5 μM to approximately 20 μM, approximately 10 μM to approximately 100 μM, or approximately 40 μM.

The cell culture composition can further comprise an FGF. In one embodiment, the FGF is bFGF. bFGF is initially present at a concentration of approximately 0.1 ng/ml to approximately 100 ng/ml, approximately 0.5 ng/ml to approximately 50 ng/ml, approximately 1 ng/ml to approximately 25 ng/ml, approximately 1 ng/ml to approximately 12 ng/ml, or is initially present at a concentration of approximately 8 ng/ml.

In a further embodiment, the cell culture medium is a conditioned medium. The conditioned medium can be obtained from a feeder layer. It is contemplated that the feeder layer comprises fibroblasts, and in one embodiment, comprises embryonic fibroblasts. In a further embodiment, the conditioned medium comprises DMEM/F-12 (50/50), approximately 20% KSR, approximately 0.1 mM NEAA, approximately 2 mM L-Glutamine, approximately 50 U/ml penicillin, approximately 50 μg/ml streptomycin, and approximately 8 ng/ml bFGF. In other embodiments, the concentration of KSR can be adjusted, or can be substituted with serum. In one embodiment, KSR is present in the conditioned medium at a concentration of approximately 2%.

It is contemplated that the methods and compositions of the invention comprise a member of the TGFβ family. In certain embodiments, the member of the TGFβ family is selected from the group consisting of Nodal, Activin A, Activin B, TGF-β, BMP2, BMP4, and mixtures of the foregoing. In certain embodiments, the member of the TGF-β family is Activin A or Nodal. It is contemplated that Activin A is initially present at a concentration of approximately 1 ng/ml to approximately 1 mg/ml, approximately 10 ng/ml to approximately 500 ng/ml, approximately 25 ng/ml to approximately 250 ng/ml, approximately 50 ng/ml to approximately 200 ng/ml, or approximately 100 ng/ml. In other embodiments, Nodal is initially present at a concentration of approximately 10 ng/ml to approximately 250 μg/ml, approximately 50 ng/ml to approximately 125 μg/ml, approximately 100 ng/ml to approximately 50 μg/ml, approximately 500 ng/ml to approximately 25 μg/ml, approximately 0.5 μg/ml to approximately 5 μg/ml or approximately 1 μg/ml.

In one embodiment, contacting the pluripotent cell with the inhibitor of the PI3-kinase pathway activates GSK3.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Examples included herein. However, before the present compositions and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989

Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

Human pluripotent cells offer unique opportunities for investigating early stages of human development as well as for therapeutic intervention in several disease states, such as diabetes mellitus and Parkinson's disease. For example, the use of insulin-producing β-cells derived from hESCs would offer a vast improvement over current cell therapy procedures that utilize cells from donor pancreases. Currently cell therapy treatments for diabetes mellitus, which utilize cells from donor pancreases, are limited by the scarcity of high quality islet cells needed for transplant. Cell therapy for a single Type I diabetic patient requires a transplant of approximately $8 \times 10^8$ pancreatic islet cells (Shapiro et al., 2000, N Engl J Med 343:230-238; Shapiro et al., 2001a, Best Pract Res Clin Endocrinol Metab 15:241-264; Shapiro et al., 2001b, Bmj 322:861). As such, at least two healthy donor organs are required for to obtain sufficient islet cells for a successful transplant. HESCs offer a source of starting material from which to develop substantial quantities of high quality differentiated cells for human cell therapies.

As used herein, the terms "biologically active component" or "bioactive component" and "bioactive factor" refer to any compound or molecule that induces a pluripotent cell to partially or terminally differentiate, wherein said differentiation is due at least in part to inhibition of signaling through the PI3-kinase pathway. While the bioactive component may be as described below, the term is not limited thereto. The term "bioactive component" as used herein includes within its scope a natural or synthetic molecule or molecules which exhibit(s) similar biological activity.

As used herein, the term "inhibitor of the PI3-kinase pathway" refers to any molecule or compound that decreases the activity of PI3-kinase or at least one molecule downstream of PI3-kinase in a cell contacted with the inhibitor. The invention encompasses, e.g., PI3-kinase antagonists, antagonists of the PI3-kinase signal transduction cascade, compounds that decrease the synthesis or expression of endogenous PI3-kinase, compounds that decrease release of endogenous PI3-kinase, and compounds that inhibit activators of PI3-kinase activity. In certain embodiments of the foregoing, the inhibitor is selected from the group consisting of Rapamycin, LY 294002, wortmannin, lithium chloride, Akt inhibitor I, Akt inhibitor II (SH-5), Akt inhibitor III (SH-6), NL-71-101, and mixtures of the foregoing. Akt inhibitor I, II, Akt III, and NL-71-101 are commercially available from Calbiochem. In other embodiments, the inhibitor is selected from the group consisting of Rapamycin and LY 294002. In a further embodiment, the inhibitor comprises LY 294002. In another embodiment, the inhibitor comprises AktI-II. In other embodiments, the inhibitor is a molecule that inhibits an upstream component of the PI3-kinase signaling pathway. In particular embodiments of the foregoing, the inhibitor is an inhibitor of an IGF or FGF receptor. It is understood that combinations of inhibitors may be used to elicit the desired effect.

In one embodiment, the pluripotent cells are contacted with an effective amount of the inhibitor of the PI3-kinase pathway. As used herein, the term "effective amount" refers to that concentration of inhibitor that is sufficient to decrease the activity of PI3-kinase or at least one molecule downstream of PI3-kinase in a cell contacted with the inhibitor and a member of the TGFβ family to effect differentiation of a pluripotent cell towards mesendoderm, and preferably towards endoderm. Alternatively, it refers to that concentration of activator that is sufficient to increase the activity of PI3-kinase or at least one molecule downstream of PI3-kinase in a cell contacted with the activator.

As used herein when referring to a cell, cell line, cell culture or population of cells, the term "isolated" refers to being substantially separated from the natural source of the cells such that the cell, cell line, cell culture, or population of cells are capable of being cultured in vitro. In addition, the term "isolating" is used to refer to the physical selection of one or more cells out of a group of two or more cells, wherein the cells are selected based on cell morphology and/or the expression of various markers.

As used herein, the term "express" refers to the transcription of a polynucleotide or translation of a polypeptide in a cell, such that levels of the molecule are measurably higher in a cell that expresses the molecule than they are in a cell that does not express the molecule. Methods to measure the expression of a molecule are well known to those of ordinary skill in the art, and include without limitation, Northern blotting, RT-PCT, in situ hybridization, Western blotting, and immunostaining.

As used herein, the term "contacting" (i.e., contacting a cell e.g. a pluripotent cell, with an compound) is intended to include incubating the compound and the cell together in vitro (e.g., adding the compound to cells in culture). The term "contacting" is not intended to include the in vivo exposure of cells to an inhibitor of the PI3-kinase pathway and the member of the TGFβ family that may occur naturally in a subject (i.e., exposure that may occur as a result of a natural physiological process). The step of contacting the cell with an inhibitor of the PI3-kinase pathway and the member of the TGFβ family can be conducted in any suitable manner. For example, the cells may be treated in adherent culture, or in suspension culture. It is understood that the cells contacted with the inhibitor of the PI3-kinase pathway and the member of the TGFβ family may be further treated with other cell differentiation environments to stabilize the cells, or to differentiate the cells further.

In one embodiment of the invention, the cells comprise an isolated nucleic acid molecule whose expression modulates signaling of the PI3-kinase pathway. In accordance with the present invention, a nucleic acid molecule can be transformed into an embryonic cell population of the present invention to inhibit or activate particular genes or gene products, thereby modulating differentiation of the cells. In one embodiment of the foregoing, the cell is an embryonic stem cell that comprises an isolated nucleic acid molecule encoding a dominant negative constitutively active form of a protein that is part of the PI3-kinase signaling pathway.

The compositions and methods described herein have several useful features. For example, the compositions and methods described herein are useful for modeling the early stages of human development. Furthermore, the compositions and methods described herein can also serve for therapeutic intervention in disease states, such as diabetes mellitus. For example, since definitive endoderm serves as the source for only a limited number of tissues, it can be used in the development of pure tissue or cell types.

A crucial stage in early human development termed gastrulation occurs 2-3 weeks after fertilization. Gastrulation is extremely significant because it is at this time that the three primary germ layers are first specified and organized (Lu et al., 2001 Curr Opin Genet Dev 11:384-392; Schoenwolf & Smith, 2000 Methods Mol Biol 135:113-125). The ectoderm is responsible for the eventual formation of the outer coverings of the body and the entire nervous system whereas the heart, blood, bone, skeletal muscle and other connective tissues are derived from the mesoderm. Definitive endoderm is defined as the germ layer that is responsible for formation of the entire gut tube which includes the esophagus, stomach and small and large intestines, and the organs which derive from the gut tube such as the lungs, liver, thymus, parathyroid and thyroid glands, gall bladder and pancreas (Grapin-Botton & Melton, 2000 Trends Genet. 16:124-130; Kimelman & Griffin, 2000, Curr Opin Genet Dev 10:350-356; Tremblay et al., 2000 Development 127:3079-3090; Wells & Melton, 1999 Annu Rev Cell Dev Biol 15:393-410; Wells & Melton, 2000 Development 127:1563-1572). A very important distinction should be made between the definitive endoderm and the completely separate lineage of cells termed primitive endoderm. The primitive endoderm is primarily responsible for formation of extra-embryonic tissues, mainly the parietal and visceral endoderm portions of the placental yolk sac and the extracellular matrix material of Reichert's membrane.

During gastrulation, the process of definitive endoderm formation begins with a cellular migration event in which mesendoderm cells (cells competent to form mesoderm or endoderm) migrate through a structure called the primitive streak. Definitive endoderm is derived from cells, which migrate through the anterior portion of the streak and through the node (a specialized structure at the anterior-most region of the streak). As migration occurs, definitive endoderm populates first the most anterior gut tube and culminates with the formation of the posterior end of the gut tube.

In vivo analyses of the formation of definitive endoderm, such as the studies in Zebrafish and *Xenopus* (Conlon et al., 1994 Development 120:1919-1928; Feldman et al., 1998 Nature 395:181-185; Zhou et al., 1993 Nature 361:543-547; Aoki et al., 2002 Dev Biol 241:273-288; Dougan et al., 2003 Development 130:1837-1851; Tremblay et al., 2000 Development 127:3079-3090; Vincent et al., 2003 Genes Dev 17:1646-1662; Alexander et al., 1999 Dev. Biol. 215:343-357; Alexander & Stainier, 1999 Curr Biol 9:1147-1157; Kikuchi et al., 2001 Genes Dev 15:1493-1505; Hudson et al., 1997 Cell 91:397-405) and in mouse (Kanai-Azuma et al., 2002 Development 129:2367-2379) lay a foundation for how one might attempt to approach the development of a specific germ layer cell type in the culture dish using human embryonic stem cells. There are two aspects associated with in vitro ESC culture that pose major obstacles in the attempt to recapitulate development in the culture dish. First, organized germ layer or organ structures are not produced. The majority of germ layer and organ specific genetic markers will be expressed in a heterogeneous fashion in the differentiating hESC culture system. Therefore it is difficult to evaluate formation of a specific tissue or cell type due to this lack of organ specific boundaries. Almost all genes expressed in one cell type within a particular germ layer or tissue type are expressed in other cells of different germ layer or tissue types as well. Without specific boundaries there is considerably less means to assign gene expression specificity with a small sample of 1-3 genes. Therefore one must examine considerably more genes, some of which should be present as well as some that should not be expressed in the particular cell type of the organ or tissue of interest. Second, the timing of gene expression patterns is crucial to movement down a specific developmental pathway.

To further complicate matters, it should be noted that stem cell differentiation in vitro is rather asynchronous, likely considerably more so than in vivo. As such, one group of cells may be expressing genes associated with gastrulation, while another group maybe starting final differentiation. Furthermore, manipulation of hESC monolayers or embryoid bodies (EBs) with or without exogenous factor application may result in profound differences with respect to overall gene expression pattern and state of differentiation. For these reasons, the application of exogenous factors must be timed according to gene expression patterns within a heterogeneous cell mixture in order to efficiently move the culture down a specific differentiation pathway.

In one embodiment, the cells treated with the inhibitor of the PI3-kinase pathway are mesendoderm cells, which can be further differentiated into mesoderm or endoderm cells. As used herein, "mesendoderm cells" are defined by the expression of one or more genes such as, but not limited to, brachyury, goosecoid, twist, Lim-1, and GATA5, which are expressed by endoderm and mesoderm precursors, however the cells do not express SOX-17. In another embodiment, the cells treated with the inhibitor of the PI3-kinase pathway are further differentiated into endoderm cells, which can be partially or terminally differentiated endoderm cells. In one embodiment, the cells treated with the inhibitor of the PI3-kinase pathway are further differentiated into cells of the definitive endoderm lineage.

As used herein, the term "endoderm" includes, but is not limited to, definitive endoderm; parietal endoderm, visceral endoderm, and mesendoderm cells. As used herein, the term "definitive endoderm" refers to early endoderm cells that have the capacity to differentiate into any or many of the endoderm cell types that are generated from the endoderm lineages in the embryo (i.e. pancreas, liver, lung, stomach, intestine and thyroid). Definitive endoderm cells are multipotent. Therefore, the use of the term "definitive endoderm" in the context of the present invention means that the cell is at least more differentiated towards an endoderm cell type than the pluripotent cell from which it is derived. Also, as used herein, producing an endoderm cell encompasses the production of a cell culture that is enriched for endoderm cells.

As used herein, "definitive endoderm" cells are characterized by the expression of specific marker transcripts such as SOX17, with the concomitant absence of marker transcripts for AFP and thrombomodulin. In addition, such cells can express MIX1, GATA4, HNFalpha, and HNF3b. Additionally, LY 294002 treatment results in the loss of a subset of cell surface CD markers initially expressed by undifferentiated hES cells, including, but not limited to, CD9, 27, 30, 46, 58 and 81. In some embodiments of the present invention, definitive endoderm cells express the SOX17 marker gene at a level higher than that of SOX7, a marker gene characteristic of visceral endoderm. Additionally, in certain embodiments, expression of the SOX17 marker gene is higher than the expression of the OCT4 marker gene, which is characteristic of hESCs. In other embodiments of the present invention, definitive endoderm cells express the SOX17 marker gene at a level higher than that of the AFP, SPARC or Thrombomodulin (TM) marker genes. In certain embodiments of the present invention, the definitive endoderm cells produced by the methods described herein do not express PDX1 (PDX1-negative). In another embodiment, the cells display similarly low expression of thrombomodulin as seen in a population of pluripotent cells as determined, for example, by flow cytometry.

In certain embodiments of the present invention, the definitive endoderm cell cultures produced by the methods described herein are substantially free of cells expressing the OCT4, SOX7, AFP, SPARC, TM, ZIC1 or BRACH marker genes. In other embodiments, the definitive endoderm cell cultures produced by the methods described herein are substantially free of cells expressing the SOX7, AFP, SPARC, TM, ZIC1 or BRACH marker genes. With respect to cells in cell cultures, the term "substantially free of" means that the specified cell type is present in an amount of less than about 5% of the total number of cells present in the cell culture.

As used herein, the term "differentiate" refers to the production of a cell type that is more differentiated than the cell type from which it is derived. The term therefore encompasses cell types that are partially and terminally differentiated.

In certain embodiments of the present invention, the term "enriched" refers to a cell culture that contains more than approximately 50%, 55%, 60%, 65%, 70%, 75%, 80%, 85%, 90%, or 95% of the desired cell lineage.

The cell types that differentiate from embryonic stem cells after contact with inhibitors of the PI3-kinase pathway and the member of the TGFβ family have several uses in various fields of research and development including but not limited to drug discovery, drug development and testing, toxicology, production of cells for therapeutic purposes as well as basic science research. These cell types express molecules that are of interest in a wide range of research fields. These include the molecules known to be required for the functioning of the various cell types as described in standard reference texts. These molecules include, but are not limited to, cytokines, growth factors, cytokine receptors, extracellular matrix, transcription factors, secreted polypeptides and other molecules, and growth factor receptors.

In one embodiment, the pluripotent cell is a human cell. As used herein, the term "pluripotent human cell" encompasses pluripotent cells obtained from human embryos, fetuses or adult tissues. In one preferred embodiment, the pluripotent human cell is a human pluripotent embryonic stem cell. In another embodiment the pluripotent human cell is a human pluripotent fetal stem cell, such as a primordial germ cell. In another embodiment the pluripotent human cell is a human pluripotent adult stem cell. As used herein, the term "pluripotent" refers to a cell capable of at least developing into one of ectodermal, endodermal and mesodermal cells. As used herein the term "pluripotent" refers to cells that are totipotent and multipotent. As used herein, the term "totipotent cell" refers to a cell capable of developing into all lineages of cells. The term "multipotent" refers to a cell that is not terminally differentiated. As also used herein, the term "multipotent" refers to a cell that, without manipulation (i.e., nuclear transfer or dedifferentiation inducement), is incapable of forming differentiated cell types derived from all three germ layers (mesoderm, ectoderm and endoderm), or in other words, is a cell that is partially differentiated. The pluripotent human cell can be selected from the group consisting of a human embryonic stem (ES) cell; a human inner cell mass (ICM)/epiblast cell; a human primitive ectoderm cell, such as an early primitive ectoderm cell (EPL); a human primordial germ (EG) cell; and a human teratocarcinoma (EC) cell. The human pluripotent cells of the present invention can be derived using any method known to those of skill in the art. For example, the human pluripotent cells can be produced using de-differentiation and nuclear transfer methods. Additionally, the human ICM/epiblast cell or the primitive ectoderm cell used in the present invention can be derived in vivo or in vitro. EPL cells may be generated in adherent culture or as cell aggregates in suspension culture, as described in WO 99/53021. Furthermore, the human pluripotent cells can be passaged using any method known to those of skill in the art, including, manual passaging methods, and bulk passaging methods such as antibody selection and protease passaging.

In certain embodiment, the embryonic stem cell of the invention has a normal karyotype, while in other embodiments, the embryonic stem cell has an abnormal karyotype. In one embodiment, a majority of the embryonic stem cells have an abnormal karyotype. It is contemplated that greater than 50%, 55%, 60%, 65%, 70%, 75%, 80%, 85%, 90% or greater than 95% of metaphases examined will display an abnormal karyotype. In certain embodiments, the abnormal karyotype is evident after the cells have been cultured for greater than 5, 6, 7, 8, 9, 10, 11, 12, 13, 14, 15, or 20 passages. In one embodiment, the abnormal karyotype comprises a trisomy of at least one autosomal chromosome, wherein the autosomal chromosome is selected from the group consisting of chromosomes 1, 7, 8, 12, 14, and 17. In another embodiment, the abnormal karyotype comprises a trisomy of more than one autosomal chromosome, wherein at least one of the more than one autosomal chromosomes is selected from the group consisting of chromosomes 1, 7, 8, 12, 14, and 17. In one embodiment, the autosomal chromosome is chromosome 12 or 17. In another embodiment, the abnormal karyotype comprises an additional sex chromosome. In one embodiment, the karyotype comprises two X chromosomes and one Y chromosome. It is also contemplated that translocations of chromosomes may occur, and such translocations are encompassed within the term "abnormal karyotype." Combinations of the foregoing chromosomal abnormalities are also encompassed by the invention.

As recited above, the invention encompasses a method of differentiating a pluripotent mammalian cell comprising: (a) providing the pluripotent mammalian cell, and (b) contacting the pluripotent mammalian cell with an effective amount of an inhibitor of the PI3-kinase signaling pathway and the member of the TGFβ family to at least partially differentiate the pluripotent cell to a cell of the endoderm lineage. In one embodiment, step (b) comprises the use of a cell differentiation environment. In another embodiment, the cells can be contacted with a cell differentiation environment after step (b).

As used herein, the term "cell differentiation environment" refers to a cell culture condition wherein the pluripotent cells are induced to differentiate, or are induced to become a human cell culture enriched in differentiated cells. Preferably, the differentiated cell lineage induced by the growth factor will be homogeneous in nature. The term "homogeneous," refers to a population that contains more than approximately 50%, 60%, 70%, 80%, 85%, 86%, 87%, 88%, 89%, 90%, 91%, 92%, 93%, 94%, 95%, 96%, 97%, 98%, or 99% of the desired cell lineage.

In one embodiment, the pluripotent cells are induced to differentiate into cells of a lineage selected from the group consisting of mesendoderm, endoderm and mesoderm lineages. In a further embodiment, the pluripotent cells are induced to differentiate into cells of the definitive endoderm lineage. Preferably, the pluripotent cells are induced to differentiate into a population comprising greater than approximately 50% definitive endoderm cells. In other embodiments, the population comprises greater than approximately 55%, 60%, 65%, 70%, 75%, 80%, 85%, 90%, 91%, 92%, 93%, 94%, 95%, 96%, 97%, 98%, or 99% of the definitive endoderm lineage.

A differentiating medium or environment may be utilized to partially, terminally, or reversibly differentiate the pluripotent cells of the present invention, either prior to, during, or after contacting the pluripotent cells with an inhibitor of PI3-kinase and the member of the TGFβ family. In accordance with the invention the medium of the cell differentiation environment may contain a variety of components including, for example, KODMEM medium (Knockout Dulbecco's Modified Eagle's Medium), DMEM, Ham's F12 medium, FBS (fetal bovine serum), FGF2 (fibroblast growth factor 2), KSR, serum, or hLIF (human leukemia inhibitory factor). The cell differentiation environment can also contain supplements such as L-Glutamine, NEAA (non-essential amino acids), P/S (penicillin/streptomycin), N2 and β-mercaptoethanol (β-ME). It is contemplated that additional factors may be added to the cell differentiation environment, including, but not limited to, fibronectin, laminin, heparin, heparin sulfate, retinoic acid, members of the epidermal growth factor family (EGFs), members of the fibroblast growth factor family (FGFs) including FGF2 and/or FGF8, members of the platelet derived growth factor family (PDGFs), antagonists of the transforming growth factor (TGF)/bone morphogenetic protein (BMP)/growth and differentiation factor (GDF) factor families including but not limited to noggin, follistatin, chordin, gremlin, cerberus/DAN family proteins, ventropin, high dose activin, and amnionless. TGF/BMP/GDF antagonists could also be added in the form of TGF/BMP/GDF receptor-Fc chimeras. Other factors that may be added include molecules that can activate or inactivate signaling through Notch receptor family, including but not limited to proteins of the Delta-like and Jagged families as well as inhibitors of Notch processing or cleavage. Other growth factors may include members of the insulin like growth factor family (IGF), insulin, the wingless related (WNT) factor family, and the hedgehog factor family. Additional factors may be added to promote mesendoderm stem/progenitor, endoderm stem/progenitor, mesoderm stem/progenitor, or definitive endoderm stem/progenitor proliferation and survival as well as survival and differentiation of derivatives of these progenitors.

In other embodiments, the cell differentiation environment comprises plating the cells in an adherent culture. As used herein, the terms "plated" and "plating" refer to any process that allows a cell to be grown in adherent culture. As used herein, the term "adherent culture" refers to a cell culture system whereby cells are cultured on a solid surface, which may in turn be coated with a solid substrate that may in turn be coated with another surface coat of a substrate, such as those listed below, or any other chemical or biological material that allows the cells to proliferate or be stabilized in culture. The cells may or may not tightly adhere to the solid surface or to the substrate. In one embodiment, the cells are plated on matrigel-coated plates. The substrate for the adherent culture may comprise any one or combination of polyornithine, laminin, poly-lysine, purified collagen, gelatin, extracellular matrix, fibronectin, tenascin, vitronectin, entactin, heparin sulfate proteoglycans, poly glycolytic acid (PGA), poly lactic acid (PLA), poly lactic-glycolic acid (PLGA) and feeder layers such as, but not limited to, primary fibroblasts or fibroblast cells lines. Furthermore, the substrate for the adherent culture may comprise the extracellular matrix laid down by a feeder layer, or laid down by the pluripotent human cell or cell culture.

The methods of the present invention contemplate that cells may be cultured with a feeder cell or feeder layer. As used herein, a "feeder cell" is a cell that is co-cultured with a target cell and stabilizes the target cell in its current state of differentiation. A feeder layer comprises more than one feeder cell in culture. In one embodiment of the above method, conditioned medium is obtained from a feeder cell that stabilizes the target cell in its current state of differentiation. Any and all factors produced by a feeder cell that allow a target cell to be stabilized in its current state of differentiation can be isolated and characterized using methods routine to those of skill in the art. These factors may be used in lieu of a feeder layer, or may be used to supplement a feeder layer.

As used herein, the term "stabilize" refers to the differentiation state of a cell. When a cell or cell population is stabilized, it will continue to proliferate over multiple passages in culture, and preferably indefinitely in culture; additionally, each cell in the culture is preferably of the same differentiation state, and when the cells divide, typically yield cells of the same cell type or yield cells of the same differentiation state. Preferably, a stabilized cell or cell population does not further differentiate or de-differentiate if the cell culture conditions are not altered, and the cells continue to be passaged and are not overgrown. Preferably the cell that is stabilized is capable of proliferation in the stable state indefinitely, or for at least more than 2 passages. Preferably, it is stable for more than 5 passages, more than 10 passages, more than 15 passages, more than 20 passages, more than 25 passages, or most preferably, it is stable for more than 30 passages. In one embodiment, the cell is stable for greater than 1 year of continuous passaging.

In one embodiment, stem cells are maintained in culture in a pluripotent state by routine passage until it is desired that they be differentiated into definitive endoderm. It is contemplated that a member of the TGFβ family is administered to the pluripotent cell in conjunction with the inhibitor of the PI3-kinase pathway. As used herein, the term "member of the TGF-β family" refers to growth factors that are generally characterized by one of skill in the art as belonging to the TGF-β family, either due to homology with known members of the TGF-β family, or due to similarity in function with known members of the TGF-β family. In certain embodiments, the member of the TGF-β family is selected from the group consisting of Nodal, Activin A, Activin B, TGF-β, BMP2, BMP4, and mixtures of the foregoing. In one embodiment, the member of the TGF-β family is Activin A. Additionally, the growth factor Wnt3a is useful for the production of definitive endoderm cells. In certain embodiments of the present invention, combinations of any of the above-mentioned growth factors can be used. It is not necessary that these components be added to the cells simultaneously.

With respect to some of the embodiments of differentiation methods described herein, the above-mentioned growth factors are provided to the cells so that the growth factors are present in the cultures at concentrations sufficient to promote differentiation of at least a portion of the stem cells to definitive endoderm. In some embodiments of the present invention, the above-mentioned growth factors are present in the cell culture at a concentration of at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml.

In certain embodiments of the present invention, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In a preferred embodiment, the growth factors are removed about four days after their addition.

Cultures of definitive endoderm cells can be grown in medium containing reduced serum or no serum. In certain embodiments of the present invention, serum concentrations can range from about 0.1% to about 20% (v/v). In some embodiments, definitive endoderm cells are grown with serum replacement. In other embodiments, definitive endoderm cells are grown in the presence of B27. In such embodiments, the concentration of B27 supplement can range from about 0.2% to about 20% (v/v) or greater than about 20% (v/v). Alternatively, the concentration of the added B27 supplement can be measured in terms of multiples of the strength of a commercially available B27 stock solution. For example, B27 is available from Invitrogen (Carlsbad, Calif.) as a 50× stock solution. Addition of a sufficient amount of this stock solution to a sufficient volume of growth medium produces a medium supplemented with the desired amount of B27. For example, the addition of 10 ml of 50×B27 stock solution to 90 ml of growth medium would produce a growth medium supplemented with 5×B27. The concentration of B27 supplement in the medium can be about 0.1×, about 0.2×, about 0.3×, about 0.4×, about 0.5×, about 0.6×, about 0.7×, about 0.8×, about 0.9×, about 1×, about 1.1×, about 1.2×, about 1.3×, about 1.4×, about 1.5×, about 1.6×, about 1.7×, about 1.8×, about 1.9×, about 2×, about 2.5×, about 3×, about 3.5×, about 4×, about 4.5×, about 5×, about 6×, about 7×, about 8×, about 9×, about 10×, about 11×, about 12×, about 13×, about 14×, about 15×, about 16×, about 17×, about 18×, about 19×, about 20× and greater than about 20×.

The progression of the hESC culture to definitive endoderm can be monitored by quantitating expression of marker genes characteristic of definitive endoderm as well as the lack of expression of marker genes characteristic of hESCs and other cell types. One method of quantitating gene expression of such marker genes is through the use of quantitative PCR (Q-PCR). Methods of performing Q-PCR are well known in the art. Other methods that are known in the art can also be used to quantitate marker gene expression. Marker gene expression can be detected by using antibodies specific for the marker gene of interest.

Using the methods described herein, compositions comprising definitive endoderm cells substantially free of other cell types can be produced. Alternatively, compositions comprising mixtures of hESCs and definitive endoderm cells can be produced. For example, compositions comprising at least 5 definitive endoderm cells for every 95 hESCs can be produced. In other embodiments, compositions comprising at least 95 definitive endoderm cells for every 5 hESCs can be produced. Additionally, compositions comprising other ratios of definitive endoderm cells to hESCs are contemplated.

In some embodiments of the present invention, definitive endoderm cells can be isolated by using an affinity tag that is specific for such cells. One example of an affinity tag specific for definitive endoderm cells is an antibody that is specific to a marker polypeptide that is present on the cell surface of definitive endoderm cells but which is not substantially present on other cell types that would be found in a cell culture produced by the methods described herein.

It is contemplated that the pluripotent cells can be dissociated to an essentially single cell culture prior to being contacted with the inhibitor of the PI3-kinase signaling pathway. As used herein, an "essentially single cell culture" is a cell culture wherein during passaging, the cells desired to be grown are dissociated from one another, such that the majority of the cells are single cells, or two cells that remain associated (doublets). Preferably, greater than 40%, 50%, 60%, 70%, 80%, 90%, 95%, 96%, 97%, 98%, 99% or more of the cells desired to be cultured are singlets or doublets. The term encompasses the use of any method known now or later developed that is capable of producing an essentially single cell culture. Non-limiting examples of such methods include the use of a cell dispersal buffer, and the use of proteases such as trypsin, collagenase, dispase, tripLE, and accutase. These proteases and combinations of certain of the proteases are commercially available. The invention contemplates that the cell culture can be dissociated to an essentially single cell culture at any point during passaging, and it is not necessary that the dissociation occur during the passage immediately prior to contact with the inhibitor. The dissociation can occur during one or more passages.

The cells produced using the methods of the present invention have a variety of uses. In particular, the cells can be used as a source of nuclear material for nuclear transfer techniques and used to produce cells, tissues or components of organs for transplant. For example, if a definitive endoderm cell is produced, it can be used in human cell therapy or human gene therapy to treat diseases such as type 1 diabetes, liver diseases, and any other diseases that affect the esophagus, stomach, small intestines, large intestines, lungs, thymus, parathyroid and thyroid glands, gall bladder and pancreas. In one embodiment of the foregoing, the definitive endoderm cell is used to treat diabetes.

Throughout this application, various publications are referenced. The disclosures of all of these publications and those references cited within those publications in their entireties are hereby incorporated by reference into this application in order to more fully describe the state of the art to which this invention pertains.

EXAMPLES

Example 1

Culture of Human ES Cells
Routine Human ES Cell Culture

The human embryonic stem cell line BG01 (BresaGen, Inc., Athens, Ga.) was used in this work. BG01 cells were grown in hES Medium, consisting of DMEM/F-12 (50/50) supplemented with 20% knockout serum replacer (KSR; Invitrogen), 0.1 mM MEM Non-essential amino acids (NEAA; Invitrogen), 2 mM L-Glutamine (Invitrogen), 50 U/ml penicillin, 50 μg/ml streptomycin (Invitrogen), 4 ng/ml bFGF (Sigma) and 0.1 mM β-mercaptoethanol (Sigma). The cells were grown on mouse primary embryonic fibroblast feeder layers that were mitotically inactivated with mitomycin C. Feeder cells were plated at $1.2 \times 10^6$ cells per 35 mm dish. The BG01 cells were passaged using a collagenase/trypsin method. Briefly, medium was removed from the dish, 1 ml of 200 U/ml Collagenase type IV (GibcoBRL) was added, and the cells were incubated at 37° C. for 1-2 minutes. Collagenase was removed and 1 ml of 0.05% trypsin/0.53 mM EDTA (GIBCO) was applied. Cells were incubated at 37° C. for 30 seconds and then washed from the feeder layer, and the trypsin was inactivated in DMEM/F-12 with 10% fetal bovine serum (FBS; Hyclone). Cells were replated on feeder layers at 100,000-300,000 cells per 35 mm dish and were passaged every 3 days.

Growth of BG01 Cells in Feeder Free Conditions hES medium (25 mls) was conditioned overnight on mitomycin treated MEFs plated in 75 cm$^2$ flasks at 56,000 cells/cm$^2$. The MEFs were used for up to 1 week with conditioned medium (CM) collection every 24 hours. CM was supplemented with an additional 8 ng/ml of hbFGF before use. Matrigel coated dishes were prepared by diluting Growth Factor Reduced BD matrigel matrix (BD Biosciences) to a final concentration of 1:30 in cold DMEM/F-12. 1 ml/35 mm dish was used to coat dishes for 1-2 hours at room temperature or at least overnight at 4° C. Plates were stored up to one week at 4° C. Matrigel solution was removed immediately before use.

Embryoid Body Formation

The BG01 cells were disaggregated using the Collagenase/trypsin method described above. Approximately 10,000 cells were suspended in 50µl of EB medium (DMEM (Cellgro) supplemented with 10% FBS (Atlanta Biolabs), 0.1 mM NEAA, 2 mM L-Glutamine, 50 U/ml penicillin and 50 µg/ml streptomycin), and were dropped onto a 100 mm Petri dish lid with a p200 pipette tip. Approximately 50 drops were placed per lid. The lid was placed onto the dish and 10 ml of PBS was placed in the dish. EBs were washed from the lid at 3 and 5 days, incubated with trypsin for 5 minutes at room temperature and disaggregated with a drawn out glass pipette. Cells were washed once in 1×PBS and fixed in 2% PFA/2% sucrose for 10 minutes at room temperature. Cells were then washed twice in PBS and stored in 1% BSA/PBS ready for antibody staining.

Example 2

Treatment of HES Cells with Inhibitors of PI3-Kinase Leads to Differentiation of the HES Cells Inhibitor Studies BG01 cells were passaged from feeders using the collagenase/trypsin method and were plated on matrigel-coated dishes at 1×10$^5$ cells/35 mm dish in conditioned medium (CM; MEF conditioned medium plus 8 ng/ml bFGF). After approximately 24 hours, the media was replaced with fresh CM, CM with inhibitor (resuspended in EtOH), CM with EtOH, or with Spontaneous Differentiation medium (hES medium minus bFGF).

In alternative methods, the BG01 cells were plated at different concentrations prior to contact with CM, CM with inhibitor and CM with EtOH Cells were plated at the following concentrations: approximately 5×10$^4$ cells/35 mm dish, approximately 1×10$^5$ cells/35 mm dish, approximately 2×10$^5$ cells/35 mm dish, approximately 4×10$^5$ cells/35 mm dish and, approximately 6×10$^5$ cells/35 mm dish.

The inhibitor LY 294002 (Biomol) was used at the concentration range approximately 20-163 µM and the inhibitor Rapamycin (Calbiochem) was used at the concentration range approximately 1.5-30 nM. LY 294002 inhibits the PI3-kinase pathway by binding to the ATP docking site of p110. Rapamycin inhibits a subset of the PI3-kinase pathway by inhibiting mTOR (mammalian target of rapamycin).

Cells were grown in these conditions for approximately 72 hours with a medium change every 24 hours. Cells were harvested using the collagenase/trypsin method for flow cytometry and RT-PCR analysis and were scraped for biochemical analysis.

By observing the cells using standard microscopy, it was noted that BG01 cells undergo morphological change when cultured in the presence of either LY 294002 or rapamycin. This morphological change is notably different from the change in cells undergoing spontaneous differentiation (FIGS. 1A-D and 2A-D). In undifferentiated cultures, individual cells were not easily discernable, being relatively small, irregular and without clearly apparent intercellular junctions at higher density. After treatment with LY 294002, however, the cells underwent marked spreading and adopted obvious epithelioid cuboidal morphologies. Individual cells were also more readily discernable at higher densities since discrete intercellular adhering junctions were evident between neighboring cells.

Additionally, in this Example, in the presence of conditioned medium, cells plated at concentrations lower than approximately 2×10$^5$ cells/35 mm dish displayed changes in morphology when contacted with LY 294002 or rapamycin. Cells plated at densities of approximately 4×10$^5$ cells/35 mm dish or higher did not demonstrate the same morphological changes upon contact with LY 294002 or rapamycin.

Example 3

Characteristics of Cells Treated with Inhibitors of PI3-Kinase

The inhibitor studies were performed as described in Example 2.

Flow Cytometry

For flow cytometry, the BG01 cells were washed with 1×PBS and fixed in 2% paraformaldehyde/1×PBS for 10 minutes at room temperature. The cells were then washed in 1×PBS and approximately 2×10$^5$ cells were incubated with primary antibody diluted in 1% BSA/1×PBS. The primary antibodies used were anti-CD9 and anti-thrombomodulin (Cymbus Biotechnology), FITC conjugated mouse monoclonal antibodies at a 1:10 dilution. Cells were incubated at 4° C. for 30 minutes and then washed twice in 1×PBS. Where appropriate, cells were resuspended in a secondary antibody, anti-mouse Alexa-488 (Molecular Probes) diluted 1:1000 in 1% BSA/PBS, incubated at 4° C. for 30 minutes, and then washed twice in 1×PBS. Cells were resuspended in 1% BSA/1×PBS and surface expression was analyzed using a Beckman Coulter FC500.

RNA Isolation and RT-PCR Analysis

Total RNA was isolated using TRIzol Reagent (Gibco-BRL). RNA was run on a 1% agarose gel containing ethidium bromide and visualized using the AlphaImager™ 2200 Documentation and Analysis System to ensure RNA integrity. 10 µg of RNA was treated with DNase (Ambion), which was removed with DNase Inactivation Reagent (Ambion). cDNA was prepared with 500 ng of total RNA using the Superscript II Reverse transcriptase Kit (Invitrogen) using oligo(dT) primers. PCR reactions were carried out on 1 µl of cDNA. PCR products were run on a 2% agarose gel containing ethidium bromide and visualized using the AlphaImager™ 2200 Documentation and Analysis System. PCR primer sets used were GATA4, Mix1, Msx1, AFP, HNF4alpha, eHAND, Nanog, AFP and GAPDH.

Biochemical Analysis

Activity of the PI3-kinase signaling pathway was assessed by Western blot analysis. Briefly, detergent extracts were prepared from untreated and treated cell cultures, separated by SDS-PAGE and blotted to nitrocellulose. Expression of active forms of the PI3-kinase intracellular targets PKB/Akt, S6 kinase and S6 protein was then determined by probing the nitrocellulose with appropriate antibodies to phosphorylated forms of each of these proteins. Generally, 30 µg of total protein was evaluated for each sample, primary incubations were carried out at a 1:1000 dilution of antibody, and binding in each case was detected by standard ECL based methodology.

Q-PCR Gene Expression Assay

Real-time measurements of gene expression were analyzed for multiple marker genes at multiple time points by Q-PCR. Marker genes characteristic of the desired as well as undesired cell types were evaluated to gain a better understanding of the overall dynamics of the cellular populations. The strength of Q-PCR analysis includes its extreme sensitivity and relative ease of developing the necessary markers, as the genome sequence is readily available. Furthermore, the extremely high sensitivity of Q-PCR permits detection of gene expression from a relatively small number of cells within a much larger population. In addition, the ability to detect very low levels of gene expression may provide indications for "differentiation bias" within the population. The bias towards a particular differentiation pathway, prior to the overt differentiation of those cellular phenotypes, would likely be unrecognizable using immunocytochemical techniques. For this reason, Q-PCR provides a method of analysis that is complementary to immunocytochemical techniques for screening the success of differentiation treatments. This tool provides a means of evaluating our differentiation protocol successes in a quantitative format at semi-high throughput scales of analysis.

The general approach was to perform relative quantitation using SYBR Green chemistry on the Rotor Gene 3000 instrument (Corbett Research) and a two-step RT-PCR format. Primers were designed to lie over exon-exon boundaries or span introns of at least 800 bp when possible, as this has been empirically determined to eliminate amplification from contaminating genomic DNA. When marker genes were employed that do not contain introns or they possess pseudogenes, DNase I treatment of RNA samples was performed. The markers relevant for the early phases of hESC differentiation (specifically ectoderm, mesoderm, definitive endoderm and extra-embryonic endoderm) and for which validated primer sets exist are provided below in Table 1. The human specificity of these primer sets has also been demonstrated. This is an important fact since the hESCs were often grown on mouse feeder layers. Most typically, triplicate samples were taken for each condition and independently analyzed in duplicate to assess the biological variability associated with each quantitative determination.

Total RNA was isolated using RNeasy (Qiagen) and quantitated using RiboGreen (Molecular Probes). Reverse transcription from 350-500 ng of total RNA was carried out using the iScript reverse transcriptase kit (BioRad), which contains a mix of oligo-dT and random primers. Each 20 µL reaction was subsequently diluted up to 100 µL total volume and 3 µL was used in each 10 µL Q-PCR reaction containing 400 nM forward and reverse primers and 5 µL 2×SYBR Green master mix (Qiagen). Two step cycling parameters were used employing a 5 second denature at 85-94° C. (specifically selected according to the melting temp of the amplicon for each primer set) followed by a 45 second anneal/extend at 60° C. Fluorescence data was collected during the last 15 seconds of each extension phase. A three point, 10-fold dilution series was used to generate the standard curve for each run and cycle thresholds (Ct's) were converted to quantitative values based on this standard curve. The quantitated values for each sample were normalized to housekeeping gene performance and then average and standard deviations were calculated for triplicate samples. At the conclusion of PCR cycling, a melt curve analysis was performed to ascertain the specificity of the reaction. A single specific product was indicated by a single peak at the $T_m$ appropriate for that PCR amplicon. In addition, reactions performed without reverse transcriptase served as the negative control and do not amplify.

Both Cyclophilin G and GUS were used to calculate a normalization factor for all samples. The use of multiple HGs simultaneously reduces the variability inherent to the normalization process and increases the reliability of the relative gene expression values (Vandesompele, et al., 2002, Genome Biol., 3: RESEARCH0034).

Q-PCR was used to determine the relative gene expression levels of many marker genes across samples receiving different experimental treatments. The marker genes employed have been chosen because they exhibit enrichment in specific populations representative of the early germ layers and in particular have focused on sets of genes that are differentially expressed in definitive endoderm and extra-embryonic endoderm. These genes as well as their relative enrichment profiles are highlighted in Table 1.

TABLE 1

| Germ Layer | Gene | Expression Domains |
| --- | --- | --- |
| Endoderm | SOX17 | definitive, visceral and parietal endoderm |
| | MIXL1 | endoderm and mesoderm |
| | GATA4 | definitive and primitive endoderm |
| | HNF3b | definitive endoderm and primitive endoderm, mesoderm, neural plate |
| | GSC | mesendoderm and definitive endoderm |
| | Cerebrus | primitive and definitive endoderm |
| Extra-embryonic | SOX7 | visceral endoderm |
| | AFP | visceral endoderm, liver |
| | SPARC | parietal endoderm |
| | TM | parietal endoderm/trophectoderm |
| | NODAL | Epiblast and anterior visceralendoderm |
| Ectoderm | ZIC1 | neural tube, neural progenitors |
| | SOX1 | neural progenitors |
| Mesoderm | BRACH | nascent mesoderm |

Immunohistochemistry

SOX17 Antibody

SOX17 is expressed throughout the definitive endoderm as it forms during gastrulation and its expression is maintained in the gut tube (although levels of expression vary along the A-P axis) until around the onset of organogenesis. SOX17 is also expressed in a subset of extra-embryonic endoderm cells. No expression of this protein has been observed in mesoderm or ectoderm. As such, SOX17 is an appropriate marker for the definitive endoderm lineage when used in conjunction with markers to exclude extra-embryonic lineages.

A SOX17 antibody was generated as described in U.S. Patent Application Publication No. 2005/0158853, entitled "Definitive Endoderm," hereby incorporated by reference in its entirety. Briefly, a portion of the human SOX17 cDNA corresponding to amino acids 172-414 in the carboxyterminal end of the SOX17 protein was used for production of SOX17 antibody by genetic immunization in rats at the antibody production company, GENOVAC (Freiberg, Germany), according to procedures developed there. Procedures for genetic immunization can be found in U.S. Pat. Nos. 5,830,876, 5,817,637, 6,165,993, 6,261,281 and International Publication No. WO99/13915, the disclosures of which are incorporated herein by reference in their entireties. The antibody was determined to be specific for SOX17 by both Western blot and ICC on hSOX17 cDNA transfected cell lines.

Cells to be immunostained were grown on chamber slides, and were rinsed once with 1×PBS and fixed for 10 minutes in 4% PFA/4% sucrose in PBS pH 7.4 at room temperature. They were then rinsed 3× in 1×PBS and blocked in 3% goat serum with 0.1% Triton-X100 in PBS for 1 hour at room temperature. Primary antibodies were diluted in 3% goat serum in PBS and this solution was applied overnight at 4° C. The primary antibodies used were rabbit anti-human AFP (Zymed), used at a 1:50 dilution, and rat anti-human SOX17 (obtained from Cythera, Inc.), used at 1:1000 dilution. Cells were washed for 1 hour with 3 changes of 1×PBS. Secondary antibodies were applied for 2 hours at room temperature. Secondary antibodies used were goat anti-rabbit Alexa Fluor 488 and goat anti-rat Alexa Fluor 594 (Molecular Probes), both at a 1:1000 dilution in 3% goat serum in 1×PBS. Cells were washed for 1 hour with 3 changes of 1×PBS. The chambers were removed and slides were mounted in VectaShield mounting medium with DAPI (Vector).

Results

Using flow cytometry, it was noted that expression of CD9 decreased more rapidly in LY 294002 or rapamycin treated BG01 cells than in spontaneous differentiation in adherent culture, or in embryoid bodies (FIGS. 3A-E). In addition, expression of CD9 has been previously observed by others to influence cell proliferation, motility and adhesion.

Figure 4A:
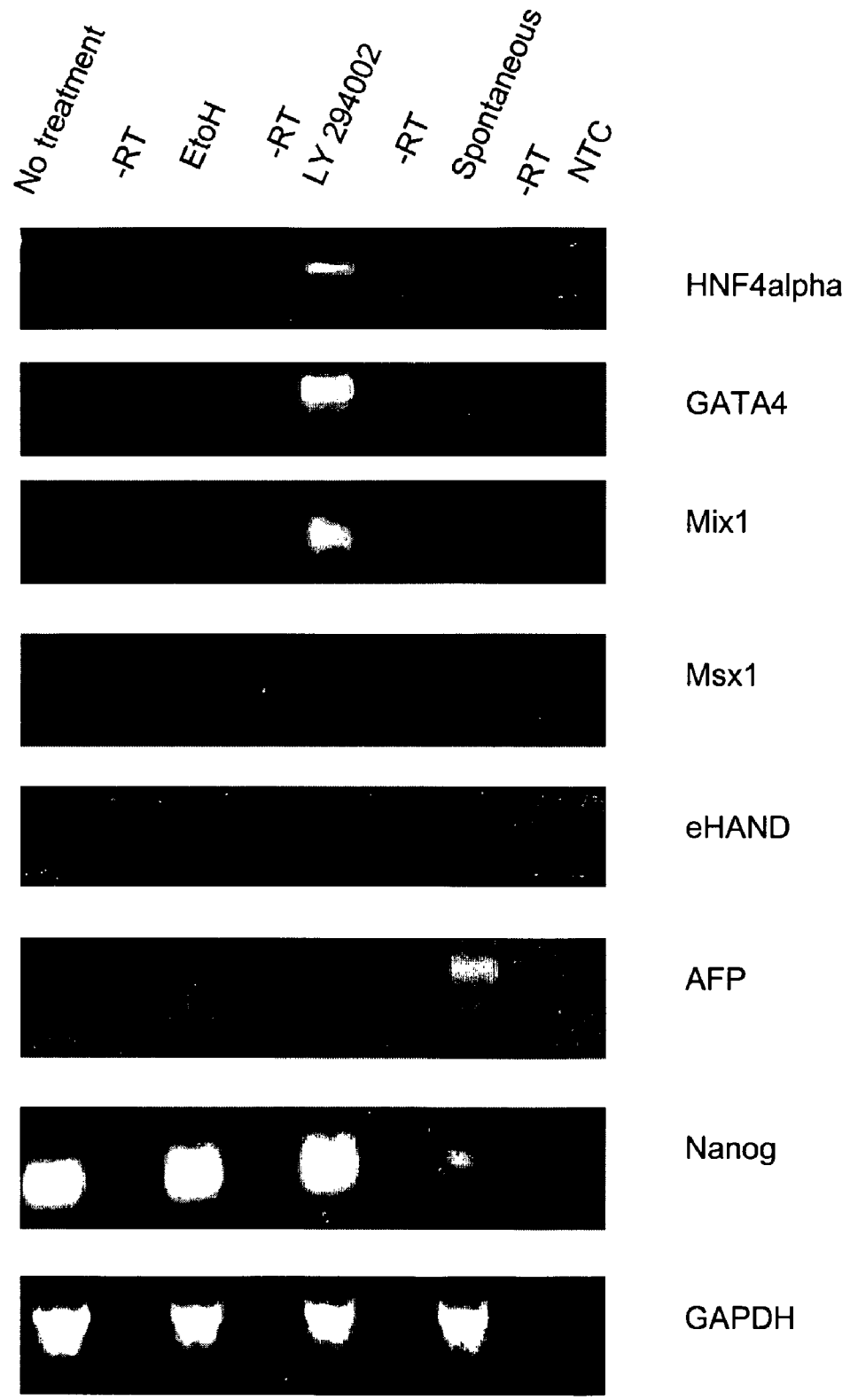
FIG. 4A shows RT-PCR analysis of lineage markers in BG01 cells, comparing expression differences between LY 294002 (80 µM) treatment and the spontaneous differentiation of the cells.
Figure 4B:
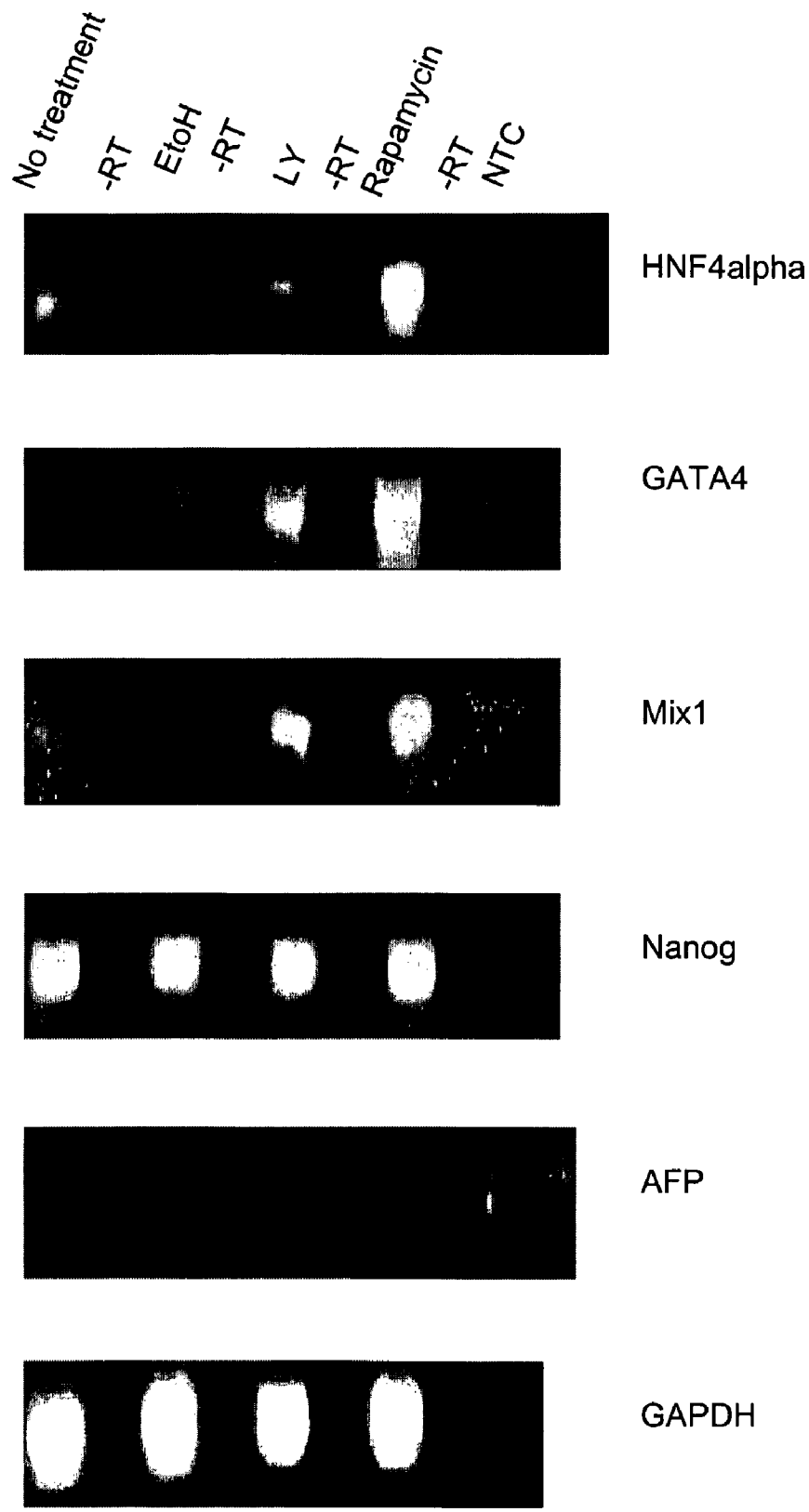
FIG. 4B shows RT-PCR analysis of lineage markers in BG01 cells, comparing expression differences between LY294002 (80 µM) and rapamycin (30 nM) treatments.

By RT-PCR analysis, it was noted that a number of markers indicative of early differentiation were detected in cells treated with LY 294002 and rapamycin (FIGS. 4A and B). Notably, the markers detected when PI3-kinase signaling was blocked differed from those detected in spontaneously differentiating adherent cultures of BG01 cells (FIGS. 4A and 4B). For example, blocking PI3-kinase resulted in an increase in levels of HNF4alpha, GATA4, Mix1, and Msx1, and a decrease in levels of AFP in comparison to spontaneously differentiating cultures.

Additionally, the differences in cell morphology that were noted with varying densities of pluripotent cells were supported by PCR data. The effect of treatment with LY 294002 or Rapamycin may in some circumstances be dependent on cell density.

Figure 5A:
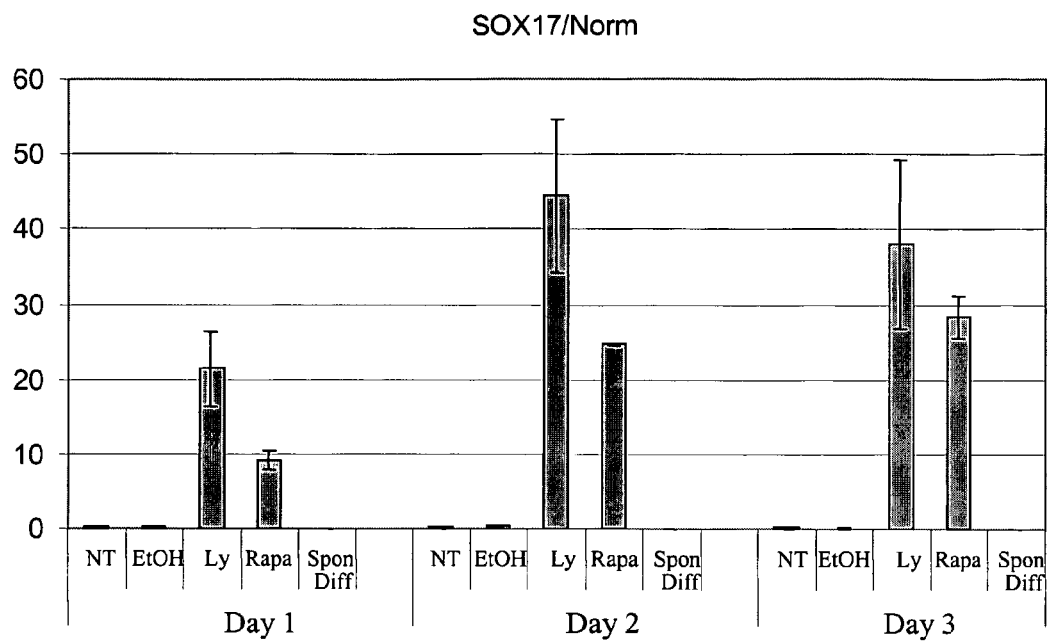
FIGS. 5A-G demonstrate that treatment of hES cell line BG01 with either LY 294002 or Rapamycin quantitatively induces the expression of genes strongly associated with mesendoderm, however, LY294002 or Rapamycin treatment do not induce expression of the pan-Neurectodermal marker SOX1, or the pan-Extraembryonic marker, SOX7. "NT" indicates untreated cells; "ETOH" indicates vehicle control; "Ly" indicates treatment with 80 µM LY 294002; "RAPA" indicates treatment with 30 nM Rapamycin; "Spon Diff" indicates spontaneous differentiation of hES cells. The figures show the relative gene expression (Y axis) as a function of treatment and time (X axis).
Figure 5B:
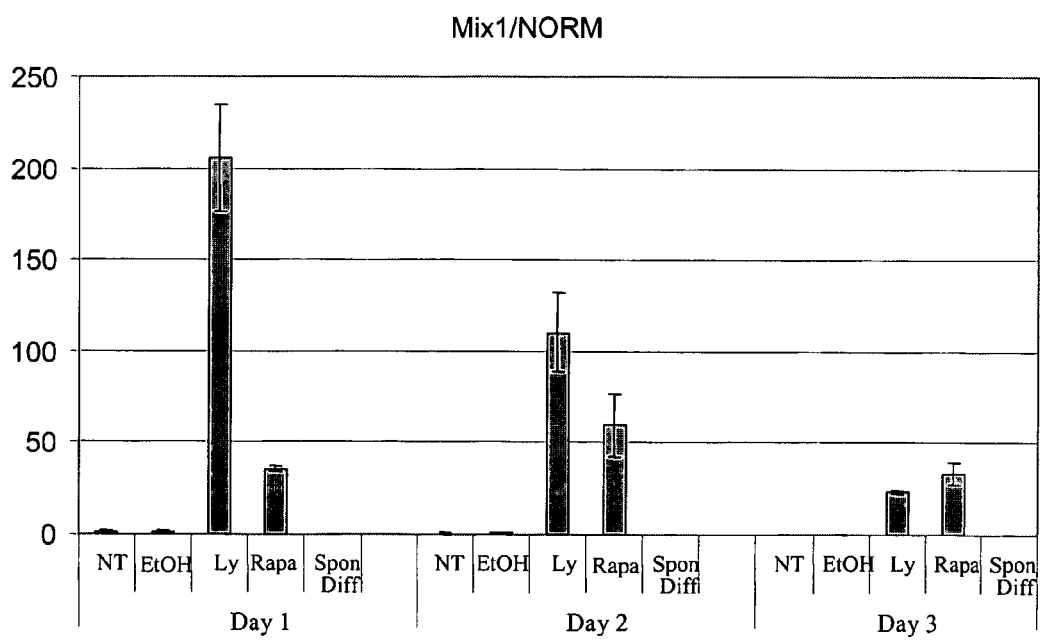
Figure 5C:
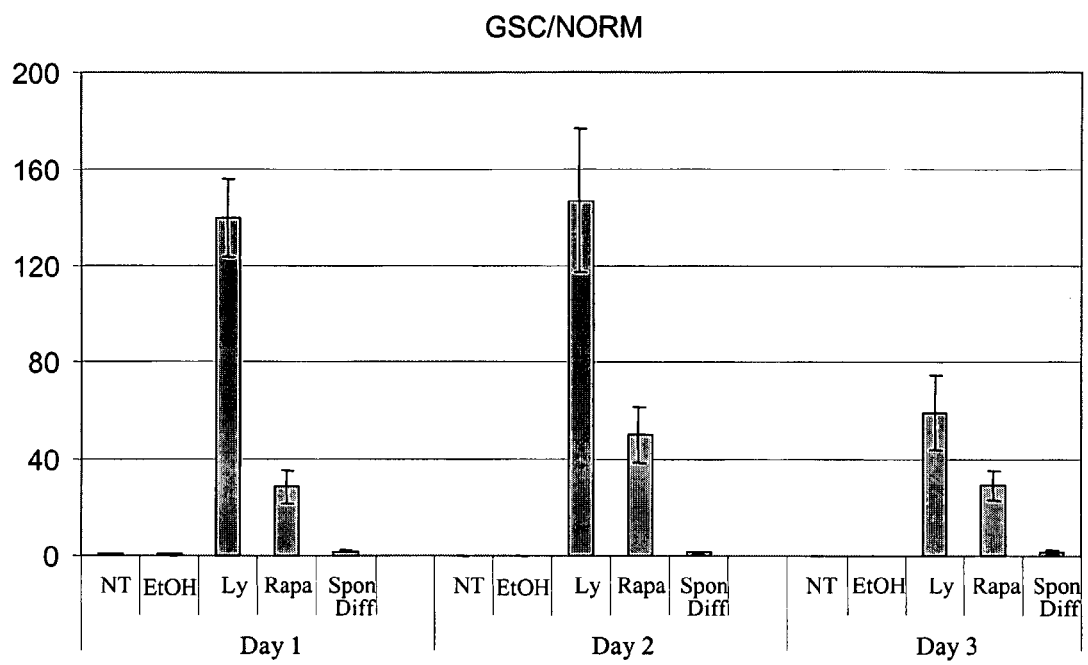
Figure 5D:
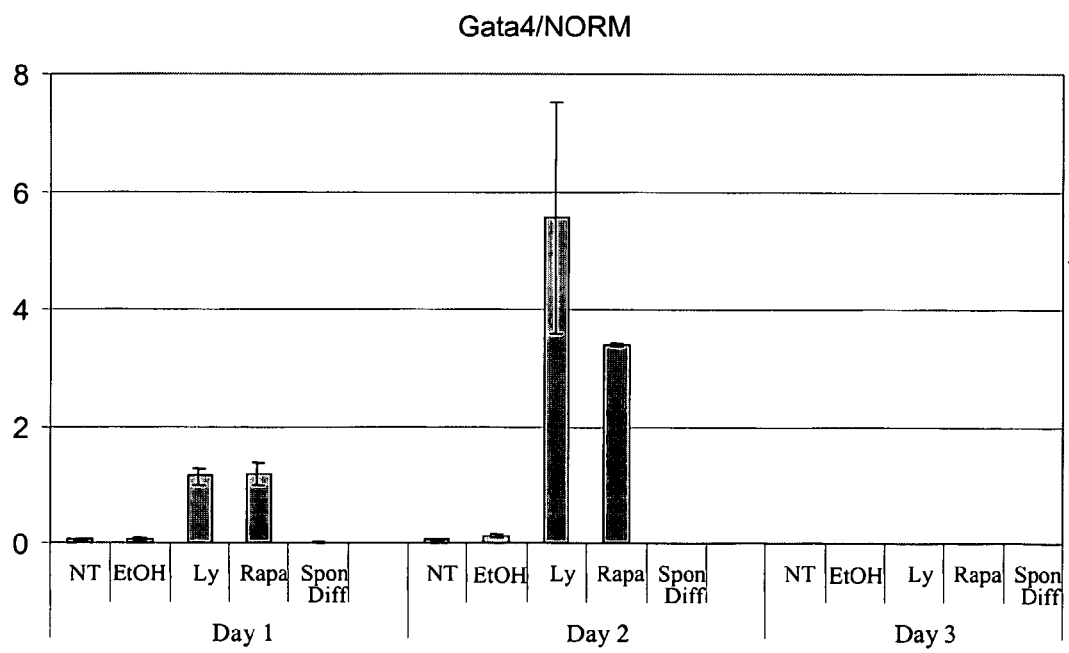
Figure 5E:
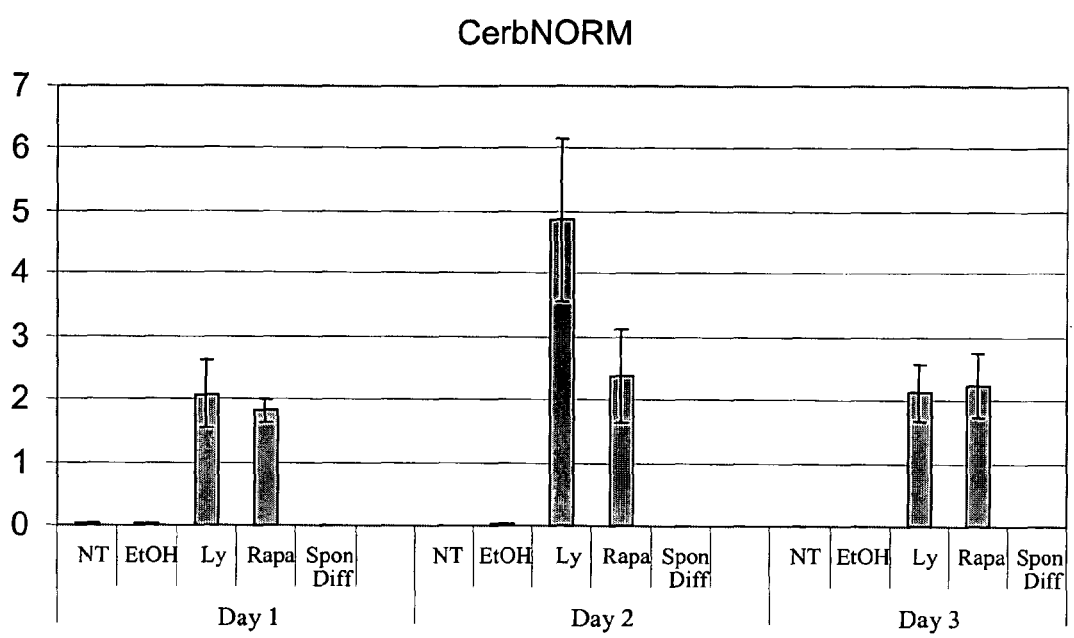
Figure 5F:
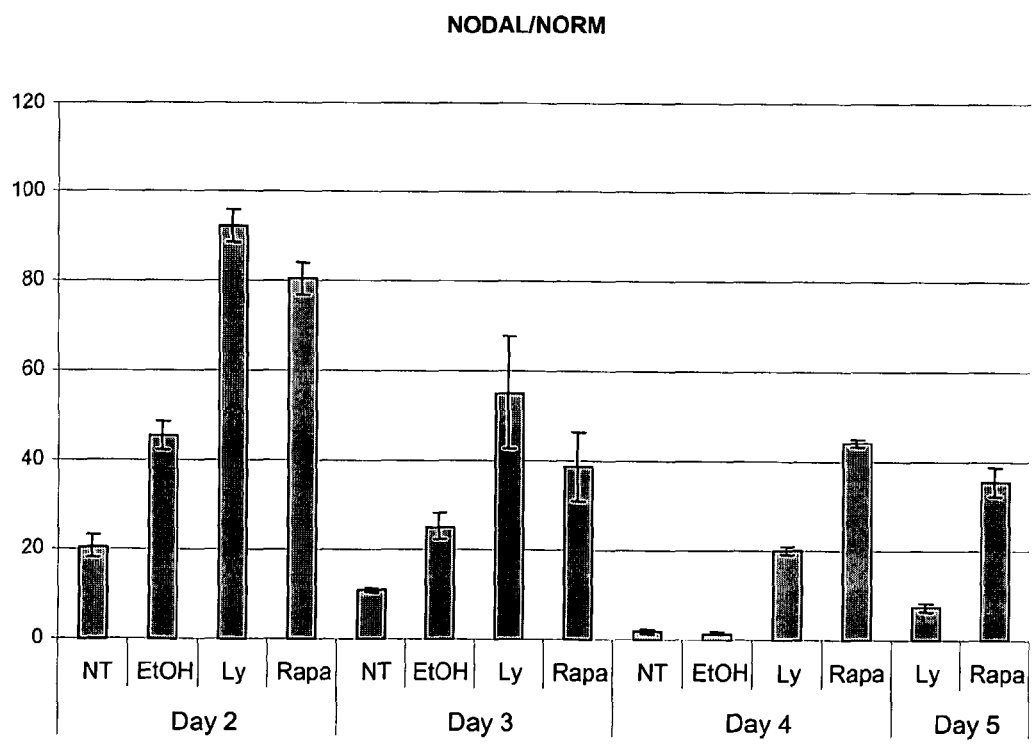
Figure 5G:
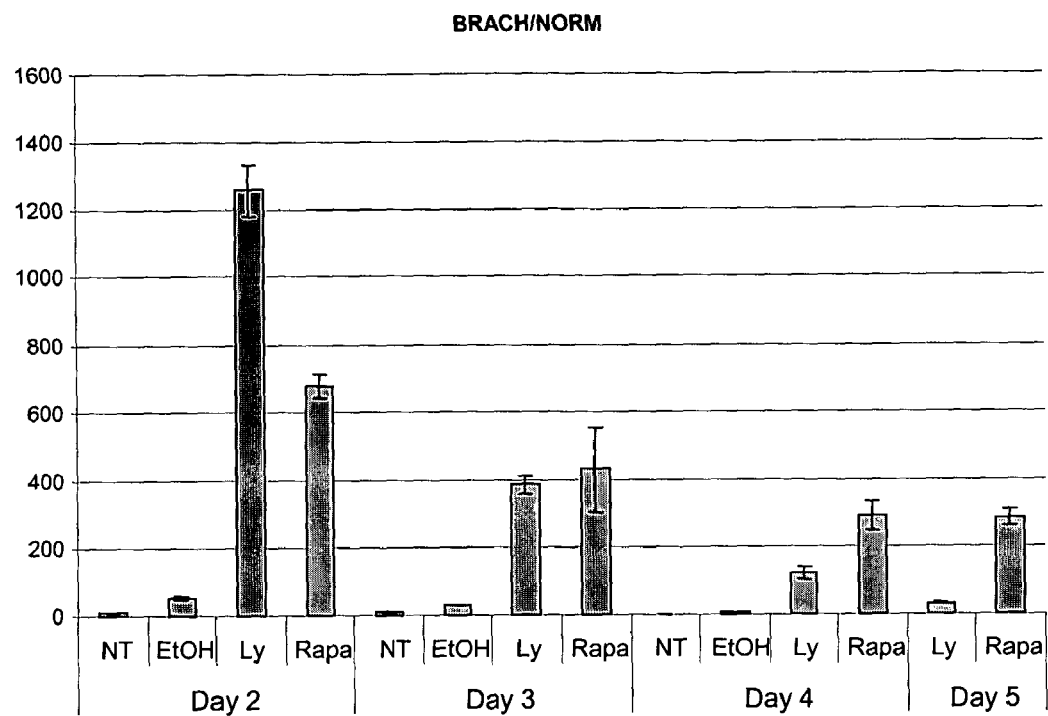
Figure 5H:
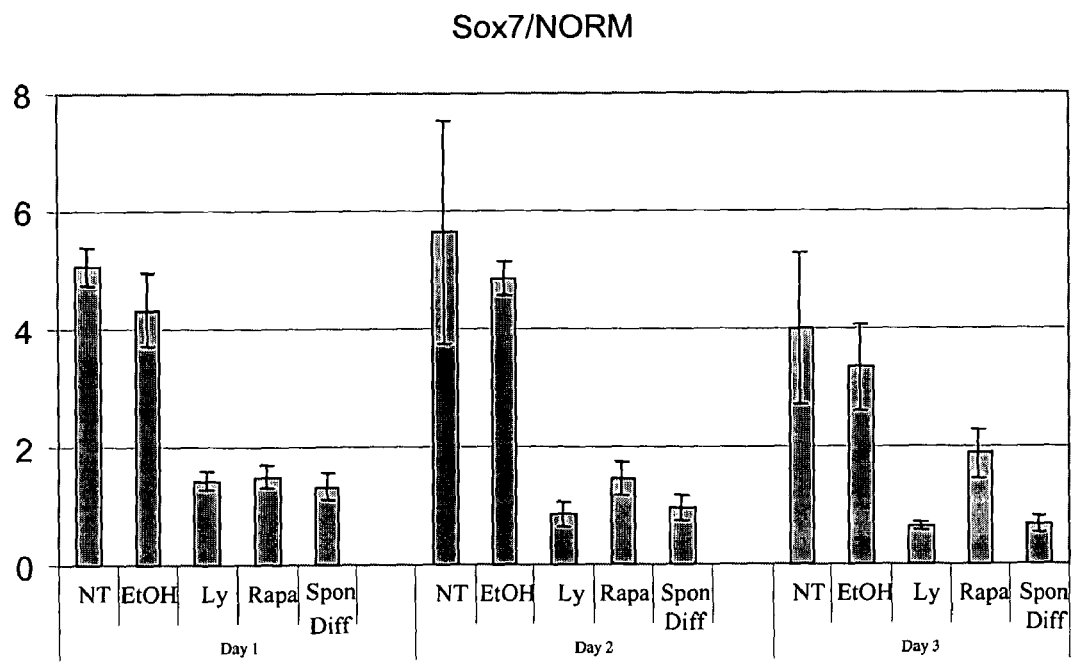
FIG. 5H shows relative SOX7 gene expression.
Figure 5I:
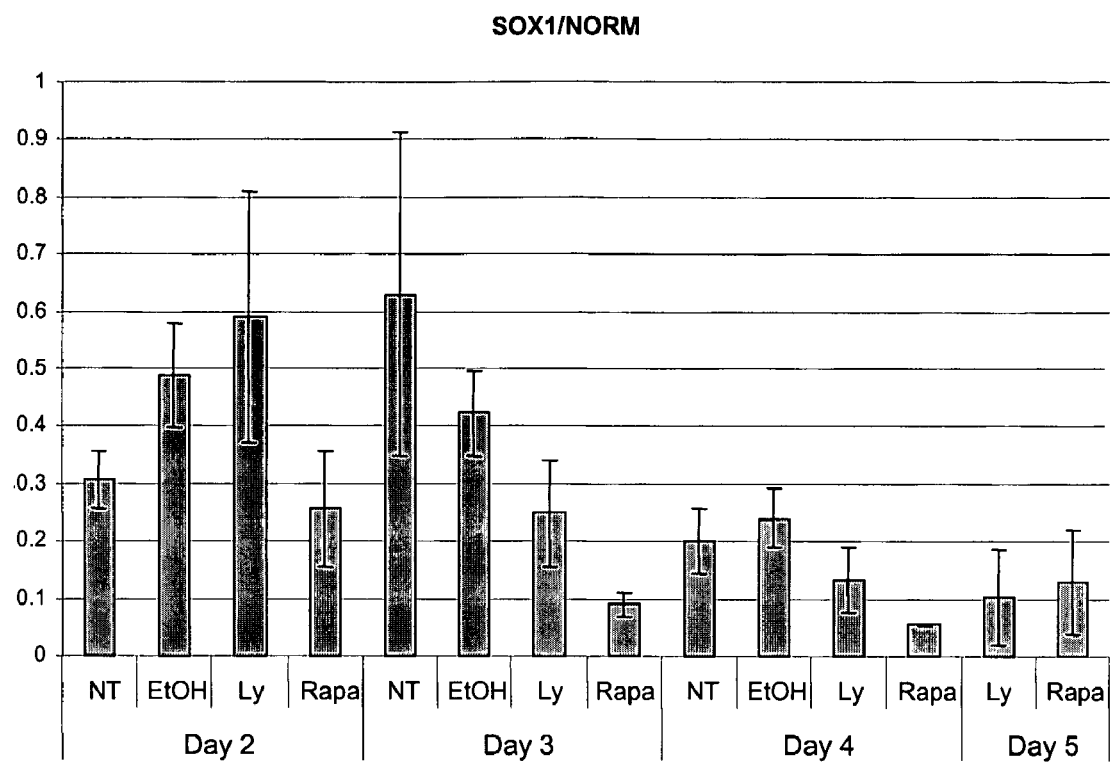
FIG. 5I shows relative SOX1 gene expression.

FIGS. 5A-G demonstrate that treatment of hES cell line BGO1 for 1-3 days with either LY 294002 or Rapamycin quantitatively induces the expression of genes strongly associated with mesendoderm (i.e., goosecoid/Brachyury/Cerebrus), the precursor to the definitive endoderm (SOX17/MIX1/goosecoid/Cerebrus) lineage. In contrast, as depicted in FIGS. 5H-5I, LY 294002 or Rapamycin do not induce expression of the pan-neurectodermal marker SOX1, or the pan-extraembryonic marker, SOX7.

In addition, SOX17 and AFP immunofluorescence staining of the BG01 cell line treated with LY 294002 (80 µM) or rapamycin (30 nM) was performed (data not shown). The double-stainings demonstrated that there is no significant expression of AFP in the treated cells. Certain fields of the cell culture did express AFP. As determined by counting 500 cells, 296 cells, or 60% of the cell population that was treated with LY 294002, expressed SOX17.

Figure 6:
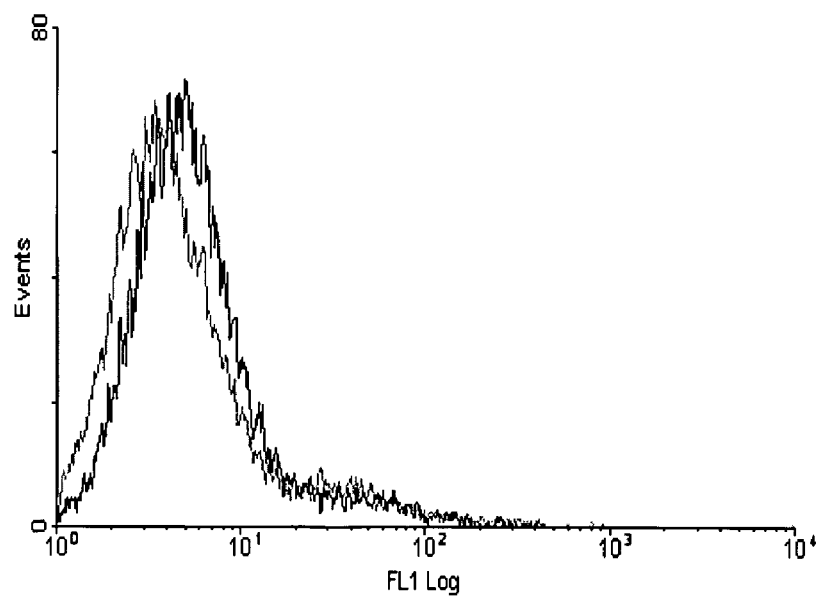
FIG. 6 shows flow cytometry analysis of thrombomodulin expression in human BG01 cells. The gray histogram shows untreated cells, while the black histogram shows cells treated with 80 µM LY 294002.

FIG. 6 shows flow cytometry analysis of thrombomodulin expression in human BG01 cells. Cells treated with 80 µM of LY 294002 demonstrate decreased levels of thrombomodulin.

Figure 7:
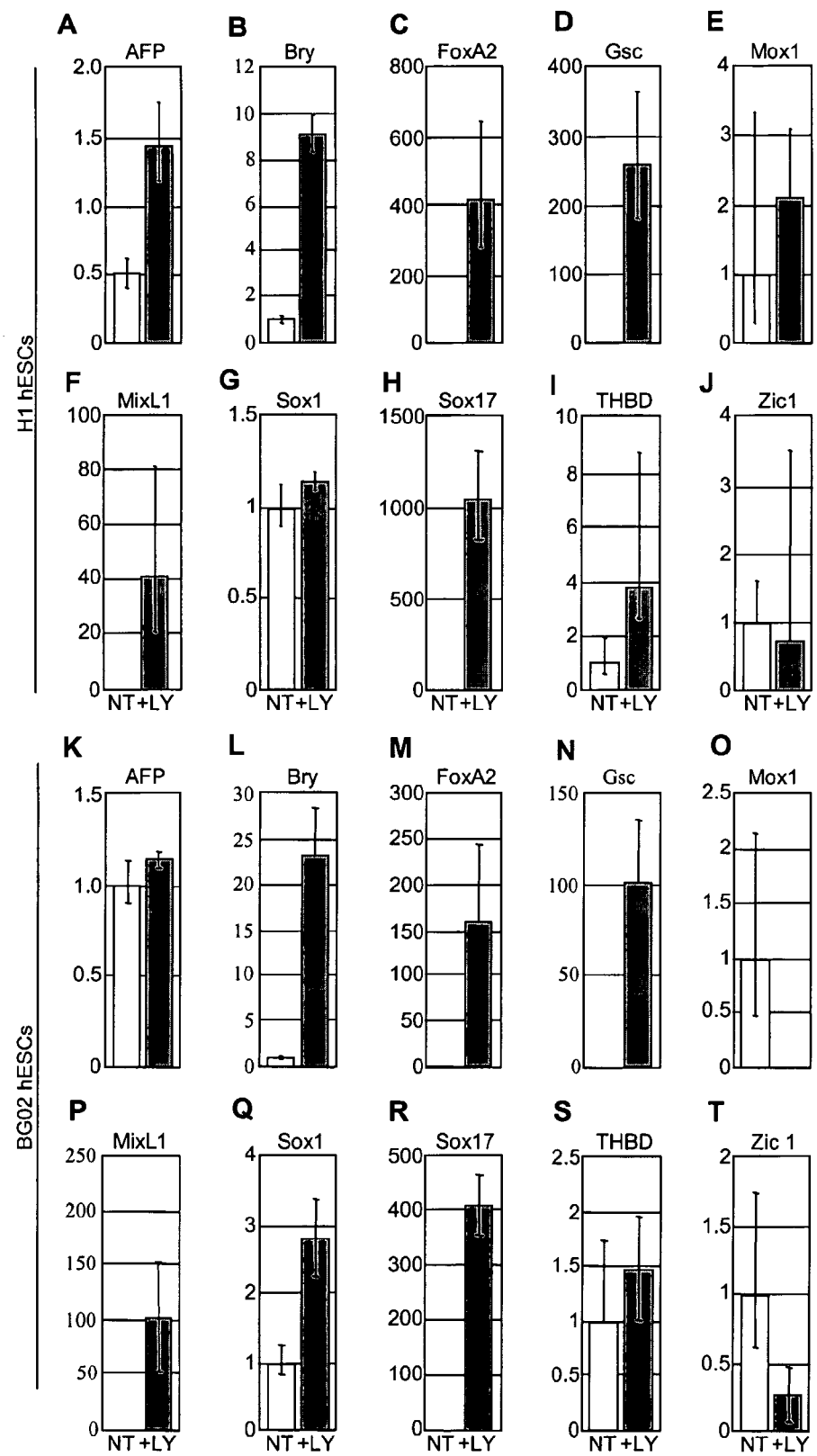
FIGS. 7A-T demonstrate that treatment of hES cell lines BG02 and H1 with LY 294002 induces the expression of genes strongly associated with mesendoderm. NT" indicates untreated cells; "LY" indicates treatment with 80 µM LY 294002. Expression levels were examined by Q-PCR after approximately 72 hours in culture with LY 294002.
FIGS. 7B and L show relative Bry expression.
FIGS. 7C and M show relative FoxA2 expression.
FIGS. 7D and N show relative GSC expression.
FIGS. 7E and O show relative Mox1 expression.
FIGS. 7F and P show relative MixL1 expression.
FIGS. 7G and Q show relative Sox1 expression.
FIGS. 7H and R show relative Sox 17 expression.
FIGS. 7I and S show relative THBD expression.
FIGS. 7J and T show relative ZIC1 expression. Assays were performed in triplicate and are shown as +/−SEM.

In addition, BG02 cells (BresaGen, Inc.) and H1 cells (WiCell) were also treated with 60 µM LY 294002 as described in Example 2. Expression of AFP, Bry, FoxA2, GSC, Mox1, MixL1, Sox1, Sox 17, THBD, and ZIC1 were examined by Q-PCR after approximately 72 hours in culture with LY 294002. As shown in FIGS. 7A-T, treatment of either line with LY 294002 results in increased levels of Sox17, MixL1, Bry, FoxA2, and GSC, while AFP, Mox1, Sox1, THBD, and ZIC1 were either not substantially increased, or showed reduced expression. These results demonstrate the repeatability of the methods of the invention using other hES cell lines. Assays were performed in triplicate and are shown as +/−SEM.

By biochemical analysis, it was noted that the activity of Akt, S6 kinase and S6 was inhibited in cells maintained in the presence of LY 294002. Similarly, the activity of S6kinase and S6 was abolished in cells maintained in the presence of rapamycin.

Collectively these observations indicate that PI3-kinase signaling to mTOR is down-regulated in BG01 cells in the presence of these inhibitory drugs. The activity of S6 (a distal target in this signaling pathway) was diminished in BG01 cells undergoing spontaneous differentiation in adherent culture, but was abolished in inhibitor treated cells.

Example 4

TGFβ Members Substitute for Conditioned Medium

Figure 8:
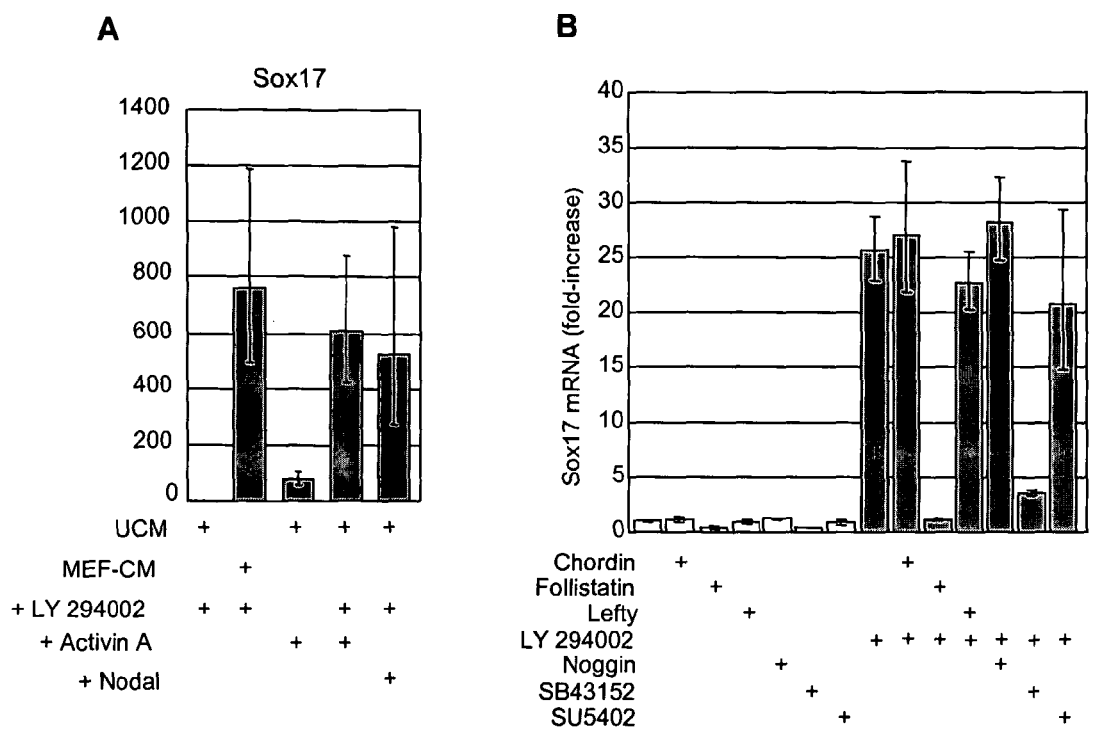
FIG. 8A shows that MEF-CM or Activin/Nodal are necessary for LY 294002-dependent hESC-DE formation. (A) shows Sox17 mRNA levels (fold-increase over untreated) as evaluated by Q-PCR under various conditions for 4 days; LY 294002 (60 µM), Activin A (100 ng/ml), Nodal (1 µg/ml). UCM indicates unconditioned media.
FIG. 8B shows LY 294002, MEF-CM dependent Sox17 expression is suppressed by inhibitors of Activin signaling but not suppressed by inhibitors of BMP or FGF signaling. Sox 17 expression was evaluated by Q-PCR under culture conditions competent to support hESC-DE formation in the presence or absence of Chordin (500 ng/ml), Follistatin (500 ng/ml), Lefty-A (500 ng/ml), Noggin (500 ng/ml), SB-43152 (10 µM), or SU-5402 (5 µM). The first column of FIG. 8B shows untreated cells. Assays were performed in triplicate and are shown as +/−SEM.

BG01 cells were passaged from feeders using the collagenase/trypsin method and were plated on matrigel coated dishes at $1\times10^5$ cells/35 mm dish in unconditioned hES medium (UCM). After approximately 24 hours, the media was replaced with fresh hES medium or MEF-CM, along with LY 294002, Activin A, or Nodal as shown in FIG. 8A. LY 294002 was used at a concentration of approximately 60 µM; Activin A was used at a concentration of approximately 100 ng/ml; and Nodal was used at a concentration of approximately 1 µg/ml. Cells were treated for approximately 4 days, with a change in medium every 24 hours. Cells were harvested using the collagenase/trypsin method for Q-PCR analysis. Sox-17 Q-PCR was performed as described in Example 3.

FIG. 8A provides Q-PCR results, showing Sox17 levels as the fold-increase over untreated cells. Significant Sox17 expression was observed in hES cells treated with (1) CM and LY 294001, (2) UCM, LY 294002, and Activin A, and (3) UCM, LY 294002 and Nodal, but not in the absence of CM, Activin or Nodal (FIG. 8A). The results indicate that MEF-CM or Activin/Nodal are necessary for LY 294002-dependent hESC-DE formation. Assays were performed in triplicate and are shown as +/−SEM.

Sox 17 expression was evaluated by Q-PCR under culture conditions competent to support hESC-DE formation (MEF-CM and LY 294002) in the presence or absence of Chordin (approximately 500 ng/ml), Follistatin (approximately 500 ng/ml), Lefty-A (approximately 500 ng/ml), Noggin (approximately 500 ng/ml), SB-43152 (approximately 10 µM), and SU-5402 (approximately 5 µM). Assays were performed in triplicate and are shown as +/−SEM. FIG. 8B shows Sox17 levels as the fold-increase over untreated cells in the various treatments, indicating that LY 294002, MEF-CM dependent Sox17 expression was suppressed by inhibitors of Activin signaling (Follistatin and SB-43152) but not by inhibitors of BMP (Chordin and Noggin), Nodal (Lefty-A) or FGF (SU-5402) signaling.

Example 5

AktI-II Induces Formation of Definitive Endoderm

BG01 cells were passaged from feeders using the collagenase/trypsin method and were plated on matrigel coated dishes at $1\times10^5$ cells/35 mm dish in conditioned medium (CM; MEF conditioned medium plus 8 ng/ml bFGF). After approximately 24 hours, the media was replaced with fresh CM, CM with inhibitor (resuspended in EtOH), or CM with EtOH.

The inhibitor AktI-II (Calbiochem) was dissolved in ethanol and was used at the concentration range approximately 10-40 μM. AktI-II inhibits the PI3-kinase pathway by directly inhibiting Akt I.

Figure 9:
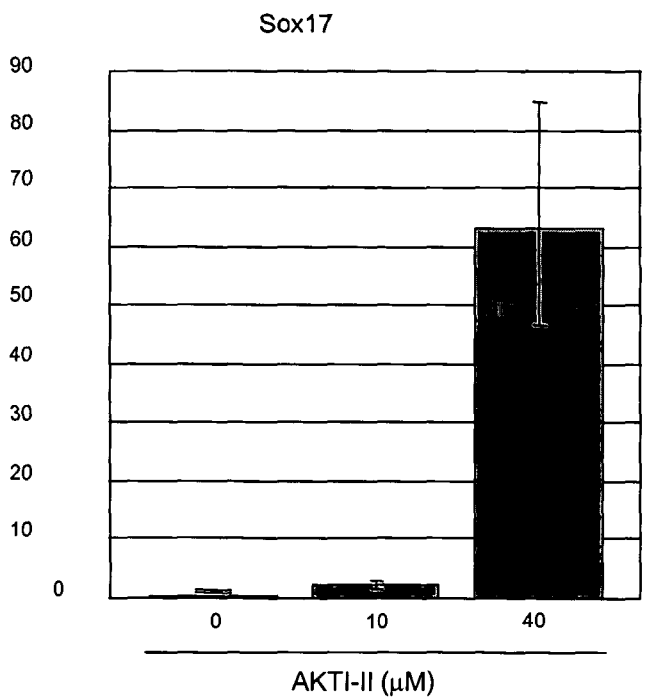
FIG. 9 shows Q-PCR results indicating that addition of approximately 40 µM of the AKT inhibitor AKT1-II can reproduce the effects of LY 294002 in promoting DE formation.

Cells were grown in these conditions for approximately 72 hours with a medium change every 24 hours. Cells were harvested using the collagenase/trypsin method for Q-PCR as described above. FIG. 9 shows Sox17 expression as a fold-increase relative to untreated hES cells.

By Q-PCR, it was ascertained that the addition of approximately 40 μM of the Akt inhibitor AKT1-II reproduces the effects of LY 294002 in promoting DE formation (FIG. 9).

Example 6

GSK3 Activation is Required for LY 294002 Induced Definitive Endoderm Formation

Since Akt phosphorylates and inhibits GSK3 activation, and since blocking Akt promotes DE formation, we investigated whether GSK3 activation is necessary for DE formation.

BG01 cells were passaged on matrigel using the collagenase/trypsin method as described above and were plated on matrigel-coated chamber slides in CM. After approximately 24 hours, the medium was changed, and the cells were treated with 60 μM LY 294002, BIO, meBIO, or DMSO for approximately 3-4 days. The inhibitor BIO (Dr. Ali Brivanlou) was diluted in DMSO and was used at a concentration of approximately 0.1-5 μM. MeBIO (Dr. Ali Brivanlou) was also diluted in DMSO and used at a concentration of approximately 1-5 μM. Assays were performed in triplicate and are shown as +/−SEM.

Figure 10:
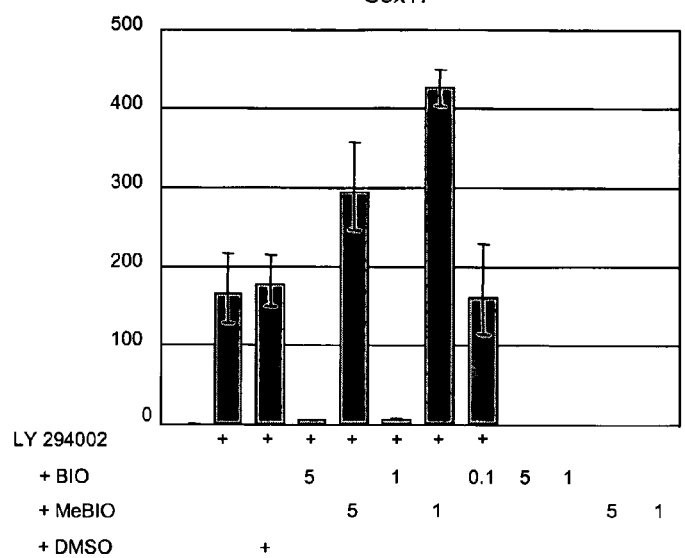
FIG. 10 shows that activation of GSK3 is required for LY 294002 to promote DE. Addition of the GSK3 inhibitor, BIO, but not MeBio, blocks LY 294002 induced DE formation. DE formation is indicated by Q-PCR analysis of the cells, showing Sox17 mRNA levels as a fold-increase over untreated cells. Assays were performed in triplicate and are shown as +/−SEM.

Cells were grown in these conditions for approximately 3-4 days with a medium change every 24 hours. Cells were harvested using the collagenase/trypsin method for Q-PCR as described above Addition of the GSK3 inhibitor, BIO, but not meBio, blocked LY 294002 induced DE formation as determined by Sox17 expression (FIG. 10).

In addition, knockdown of GSK3 expression with two specific RNAi molecules, but not a mutant RNAi, blocks the ability of LY 294002 to promote DE formation. BG01 cells were passaged from feeders using the collagenase/trypsin method and were plated on matrigel coated chamber slides in . . . CM. After approximately 24 hours, the medium was changed, and the cells were transfected with various RNAi sequences. The cells were transfected with 100 nM of the RNAi duplexes with Lipofectamine 2000 (Invitrogen). GSK3β wild-type 1 and 2 were purchased from Invitrogen (GSK3beta Validated RNAi DuoPack; #45-1488) as was the control mutant RNAi (Invitrogen, #46-2001).

12 hours after transfection, LY 294002 was added to all wells. The medium was changed daily. Cells were grown in these conditions for approximately 1-4 days, and the cells were subsequently fixed and immunostained at days 1, 2, 3, and 4 as indicated in FIGS. 11A and B.

Cells to be immunostained were rinsed once with 1×PBS and fixed for 10 minutes in 4% PFA/4% sucrose in PBS pH 7.4 at room temperature. They were then rinsed 3× in 1×PBS and blocked in 3% goat serum with 0.1% Triton-X100 in PBS for 1 hour at room temperature. Primary antibodies were diluted in 3% goat serum in PBS and this solution was applied overnight at 4° C. The primary antibodies used were pan GSK (BD Biosciences, Cat. #610202), used at a 1:1000 dilution and rat anti-human SOX17 (obtained from Cythera, Inc.), used at 1:1000 dilution. Cells were washed for 1 hour with 3 changes of 1×PBS. Secondary antibodies were applied for 2 hours at room temperature. Secondary antibodies used were goat anti-rabbit Alexa Fluor 488 and goat anti-rat Alexa Fluor 594 (Molecular Probes), both at a 1:1000 dilution in 3% goat serum in 1×PBS. Cells were washed for 1 hour with 3 changes of 1×PBS. The chambers were removed and slides were mounted in VectaShield mounting medium with DAPI (Vector). Greater than 200 cells per sample were scored, and assays were performed in duplicate.

Figure 11:
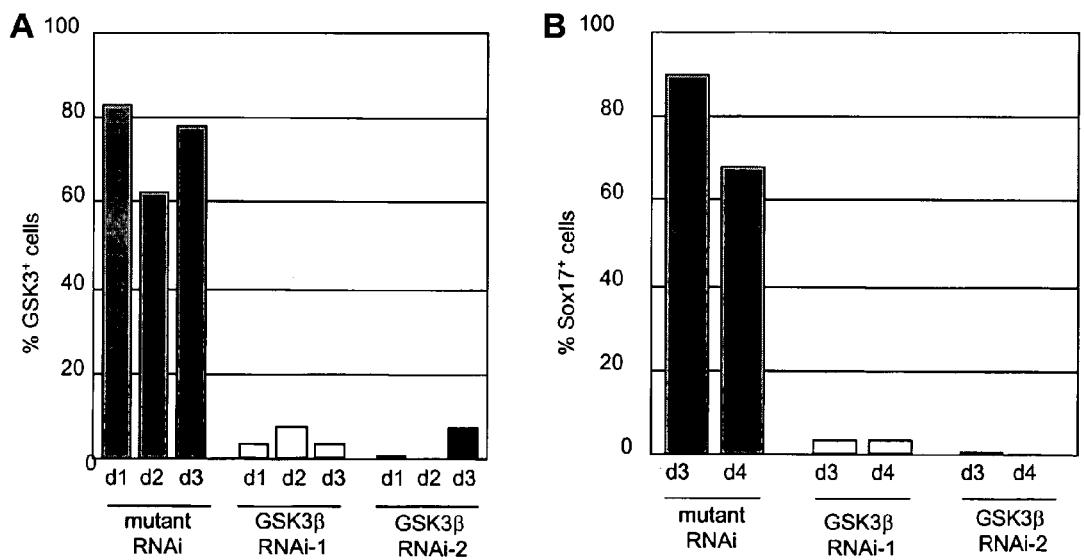
FIGS. 11A and B show that knockdown of GSK3 expression with two specific RNAi molecules, but not a mutant RNAi, blocks the ability of LY 294002 to promote DE formation. Cells were assayed by GSK3 and Sox17 immunocytochemistry at the times indicated.

FIGS. 11A and B show the percentage of GSK3 and Sox17 positive cells, respectively, upon treatment with the different RNAi molecules. Treatment with the GSK3 specific RNAi sequences decreased expression of both GSK3 and Sox17, while treatment with the control RNAi sequence did not decrease expression of either GSK3 or Sox17. Therefore, GSK3 activation is necessary for the induction of DE by LY 294002.

These results indicate that the endogenous activity of PI3-kinase and a member of the TGFβ family may be necessary for the pluripotency of human ES cells, and that pharmacological inhibition of PI3-kinase activity in self-renewing populations results in a biological commitment to multilineage differentiation in vitro. These data indicate that commitment to differentiation to definitive endoderm in human ES cells may be controlled by the level of endogenous PI3-kinase, and that this pivotal signaling axis must be silenced for the onset of differentiation to definitive endoderm to occur in vitro. Suppression of this kinase activity has been achieved with highly specific, potent and well documented pharmacological inhibitors, LY 294002 in the case of PI3-kinase (Pullen & Thomas, (1997) FEBS Lett., 410: 78-82), rapamycin in the case of mTOR (Han et al., (1995) J. Biol. Chem., 21396-21403), and AktI-II in the case of Akt I. The optimal effective concentrations for initiating human ES cell differentiation in vitro by each of these inhibitors has been established. Ongoing studies are aimed at defining the subset of serum factors other than TGFβ family members that are essential for maintaining the endogenous activation of both PI3-kinase and p70 S6 kinase in the context of human ES in vitro pluripotency.

Example 7

Kidney Capsule Assays of LY 294002 Induced Definitive Endoderm Cells

Untreated hESCs or hESCs treated for 4 days with 60 μM LY 294002 were collagenase treated to generate cell aggregates (~50 cells/aggregate), washed in warm media, then gently resuspended in 2 ml DMEM/F12, 10% FCS and left overnight at 37° C., 10% $CO_2$ to facilitate further aggregation. Approximately $2.5 \times 10^6$ cells were injected into the kidney capsule of 5 week old male SCID-beige mice. 6 weeks after transplantation, mice were sacrificed, and the kidneys were removed and fixed in 4% paraformaldehyde. Following fixation, kidneys were embedded in paraffin wax, sectioned and mounted onto glass slides in preparation for H&E and immunostaining. After mounting, slides underwent deparaffinization, rehydration and heat induced epitope retrieval with Trilogy (Cell Marque, CMX-833). Slides were stained using the alkaline phosphatase Vectastain ABC System (Vector Labs, AK-5002) and Vector Red substrate (Vector Labs, SK-5100). The following antibodies were used for immunocytochemistry, albumin (Sigma, A0433), AFP (Cell Marque, CMC700), Gastrin (CMC106), HSF (Cell Marque, CMC773), LFABP (Fitzgerald Industries International, RDI-FABP-L2E3), TTF-1 (Cell Marque, CMC572), Villin (Cell Marque, CMC833). For fluorescence immunocytochemistry the following secondary antibodies were used; Alexa Fluor 488 goat anti-mouse IgG (Molecular Probes, A11001), Alexa Fluor 594 goat anti-rabbit IgG (Molecular Probes, A11012).

FIG. 12A shows that LY 294002 treated hESCs formed a large mass on the kidney (right panel), which is striking in comparison to a kidney that did not contain an implant (left panel).

FIGS. 12B-G show photomicrographs of immunostainings of LY 294002 treated aggregates after culture under a kidney capsule for approximately 6 weeks. The aggregates express TTF-1 (B), AFP (C), villin (D), gastrin (E), HSA (F) and LFABP (G), indicating that the LY 294002 treated cells differentiate to derivatives of endoderm. The expression of LFABP and albumin were largely co-localized (data not shown). Additionally, FIGS. 12H and 12I show Q-PCR results, showing a 1000-fold increase in FABP1 mRNA and a 4500-fold increase in albumin mRNA in LY294002 treated HESCs relative to LY 294002 treated HESCs that were not implanted. Assays were performed in triplicate and are shown as +/−SEM.

We claim:

1. A method of differentiating a pluripotent human embryonic stem cell culture, the method consisting essentially of the steps:
    (a) providing the pluripotent human embryonic stem cell culture, and
    (b) contacting the pluripotent human embryonic stem cell culture with an effective amount of an inhibitor of a PI-3-kinase signaling pathway and a member of the TGFβ family to differentiate pluripotent human embryonic stem cells to definitive endoderm cells,
    wherein the inhibitor of a PI-3-kinase signaling pathway and the member of the TGFβ family are added exogenously to the pluripotent human embryonic stem cell culture at the same time,
    wherein the member of the TGFβ family is selected from the group consisting of Nodal, Activin A, Activin B, TGF-β, BMP2, BMP4, and a mixture thereof,
    thereby producing a definitive endoderm cell culture, wherein the percentage of definitive endoderm cells in the definitive endoderm cell culture is greater than 50%.

2. The method of claim 1, wherein the pluripotent human embryonic stem cell culture is contacted with the inhibitor and the member of the TGFβ family for greater than approximately 24 hours.

3. The method of claim 1, wherein GSK3 is activated.

4. The method of claim 1, wherein the inhibitor is selected from the group consisting of LY 294002, Rapamycin, wortmannin, lithium chloride, Akt inhibitor I, Akt inhibitor II, Akt inhibitor III, NL-71-101, and mixtures of the foregoing.

5. The method of claim 1, wherein the inhibitor is LY 294002.

6. The method of claim 5, wherein LY 294002 is initially present at a concentration of approximately 1 µM to approximately 500 µM.

7. The method of claim 5, wherein LY 294002 is initially present at a concentration of approximately 20 µM to approximately 163 µM.

8. The method of claim 1, wherein the inhibitor is Rapamycin.

9. The method of claim 8, wherein Rapamycin is initially present at a concentration of approximately 0.1 nM to approximately 500 nM.

10. The method of claim 8, wherein Rapamycin is initially present at a concentration of approximately 1.5 nM to approximately 30 nM.

11. The method of claim 1, wherein the inhibitor is AktI-II.

12. The method of claim 11, wherein Akt inhibitor II is initially present at a concentration of approximately 10 µM to approximately 50 µM.

13. The method of claim 1, wherein steps (b) and (c) occur in the presence of bFGF.

14. The method of claim 13, wherein bFGF is initially present at a concentration of approximately 1 ng/ml to approximately 12 ng/ml.

15. The method of claim 1, wherein the member of the TGFβ family is Activin A.

16. The method of claim 1, wherein the pluripotent human embryonic stem cell is dissociated to an essentially single cell culture prior to contacting the pluripotent human embryonic stem cell with the inhibitor.

17. The method of claim 16, wherein the cell is dissociated using a protease.

18. The method of claim 17, wherein the protease is trypsin.

19. The method of claim 1, wherein the pluripotent human embryonic stem cell is plated prior to contact with the PI-3-kinase inhibitor and the member of the TGFβ family.

* * * * *